(12) United States Patent
Baum et al.

(10) Patent No.: US 11,999,799 B2
(45) Date of Patent: Jun. 4, 2024

(54) ANTI-TMPRSS2 ANTIBODIES AND ANTIGEN-BINDING FRAGMENTS

(71) Applicant: Regeneron Pharmaceuticals, Inc., Tarrytown, NY (US)

(72) Inventors: Alina Baum, Pleasantville, NY (US); Christos Kyratsous, Irvington, NY (US); Lisa Purcell, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 74 days.

(21) Appl. No.: 17/171,941

(22) Filed: Feb. 9, 2021

(65) Prior Publication Data
US 2021/0246226 A1 Aug. 12, 2021

Related U.S. Application Data

(60) Provisional application No. 63/094,199, filed on Oct. 20, 2020, provisional application No. 63/021,016, filed on May 6, 2020, provisional application No. 62/972,338, filed on Feb. 10, 2020.

(51) Int. Cl.
| | | |
|---|---|---|
| C07K 16/40 | (2006.01) | |
| A61K 39/39 | (2006.01) | |
| A61K 39/395 | (2006.01) | |
| A61K 45/06 | (2006.01) | |
| C12N 9/50 | (2006.01) | |

(52) U.S. Cl.
CPC .......... *C07K 16/40* (2013.01); *A61K 39/3955* (2013.01); *A61K 45/06* (2013.01); *C12N 9/50* (2013.01); *C07K 2317/31* (2013.01); *C07K 2317/33* (2013.01); *C07K 2317/92* (2013.01)

(58) Field of Classification Search
CPC ................ C07K 16/40; C07K 2317/92; C07K 2317/21; A61K 39/3955; A61K 45/06
See application file for complete search history.

(56) References Cited

U.S. PATENT DOCUMENTS

| | | |
|---|---|---|
| 4,399,216 A | 8/1983 | Axel et al. |
| 4,740,461 A | 4/1988 | Kaufman et al. |
| 4,816,567 A | 3/1989 | Cabilly et al. |
| 4,912,040 A | 3/1990 | Kaufman et al. |
| 4,952,496 A | 8/1990 | Studier et al. |
| 4,959,455 A | 9/1990 | Clark et al. |
| 5,693,489 A | 12/1997 | Studier et al. |
| 5,789,215 A | 8/1998 | Berns et al. |
| 6,596,541 B2 | 7/2003 | Murphy et al. |
| 7,582,298 B2 | 1/2009 | Stevens et al. |
| 8,502,018 B2 | 8/2013 | Murphy et al. |
| 9,498,529 B2 | 11/2016 | Purcell Ngambo |
| 2017/0355756 A1* | 12/2017 | Julien .................... A61P 25/00 |

FOREIGN PATENT DOCUMENTS

| | | | |
|---|---|---|---|
| WO | WO 2002004953 A2 | 1/2002 | |
| WO | WO 2008020079 | 2/2008 | |
| WO | WO-2008068048 A2 * | 6/2008 | .............. A61P 31/10 |
| WO | WO 2008127347 A1 | 10/2008 | |
| WO | WO 2009138519 | 11/2009 | |
| WO | WO 2014022540 A1 | 2/2014 | |
| WO | WO 2015179535 A1 | 11/2015 | |
| WO | WO 2016100807 A2 | 11/2016 | |
| WO | WO 2017151453 A1 | 9/2017 | |
| WO | WO 2019147831 A1 | 8/2019 | |

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie et al., A single engineered amino acid substitution changes antibody fine specificity. J Immunol. Jan. 1, 1994;152(1): 146-52. (Year: 1994).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

Iwata-Yoshikawa et al. (2019) "TMPRSS2 Contributes to Virus Spread and Immunopathology in the Airways of Murine Models after Coronavirus Infection", Journal of Virology, 93(6):e01815-e01818, 15 pages.

International Search Report and Written Opinion for International Application No. PCT/US2021/017290 dated May 25, 2021, 15 pages.

Thorpe (1984) "Antibody Carriers Of Cytotoxic Agents In Cancer Therapy: A Review", Monoclonal Antibodies '84: Biological and Clinical Applications: Proceedings of the International Symposium on Monoclonal Antibodies held in Florence, Italy, Oct. 16-19, 1984, eds. Pinchera et al., 475-506.

Arnon et al. (1985) "Monoclonal Antibodies for Immunotargeting Of Drugs In Cancer Therapy", Monoclonal Antibodies And Cancer Therapy, Reisfeld et al. (eds.), pp. 243-256.

Berry et al. (2014) "Passive Broad-Spectrum Influenza Immunoprophylaxis", Influenza Res Treat., 2014:267594. Epub Sep. 22, 2014.

(Continued)

*Primary Examiner* — Aurora M Fontainhas
*Assistant Examiner* — Jennifer A Benavides
(74) *Attorney, Agent, or Firm* — FisherBroyles, LLP; Cara L. Crowley-Weber; Gabriele Amodeo

(57) ABSTRACT

The present disclosure provides antibodies and antigen-binding fragments thereof that bind specifically to TMPRSS2 and methods of using such antibodies and fragments for treating or preventing viral infections (e.g., coronavirus infections or influenza virus infections).

44 Claims, No Drawings

Specification includes a Sequence Listing.

(56) References Cited

OTHER PUBLICATIONS

Bertram et al. (2010) "TMPRSS2 and TMPRSS4 Facilitate Trypsin-Independent Spread of Influenza Virus in Caco-2 cells", Journal of Virology, 84(19): 10016-10025.
Bottcher et al. (2006) "Proteolytic Activation of Influenza Viruses by Serine Proteases TMPRSS2 and HAT from Human Airway Epithelium", Journal of Virology, 80(19):9896-9898.
Bottcher-Friebertshauser et al. (2011) "Inhibition of Influenza Virus Infection in Human Airway Cell Cultures by an Antisense Peptide-Conjugated Morpholino Oligomer Targeting the Hemagglutinin-Activating Protease TMPRSS2", Journal of Virology, 85:1554-1562.
Chothia et al. (1987) "Canonical Structures for the Hypervariable Regions of Immunoglobulins", J Mol. Biol., 196:901-917.
Chothia et al. (1989) "Conformations of Immunoglobulin Hypervariable Regions", Nature, 342:878-883.
Ehring (1999) "Hydrogen Exchange/Electrospray Ionization Mass Spectrometry Studies of Structural Features of Proteins and Protein/Protein Interactions", Analytical Biochemistry, 267:252-259.
Engen and Smith (2001) "The Basics of Ion Chromatography", Anal. Chem., 73: 256A-265A.
Esumi et al. (2015) "Transmembrane Seine Protease TMPRSS2 Activates Hepatitis C Virus Infection", Hepatology, 61 (2): 437-446.
GenBank as accession No. FJ966082.1 , 2009.
Gonnet et al. (1992) "Exhaustive Matching of the Entire Protein Sequence Database", Science 256: 1443-1445.
Heurich et al. (2014) TMPRSS2 and ADAM17 Cleave ACE2 Differentially and Only Proteolysis by TMPRSS2 Augments Entry Driven by the Severe Acute Respiratory Syndrome Coronavirus Spike Protein, Journal of Virology, 88 (2):1293-1307.
Abe et al. (2013) "TMPRSS2 Is an Activating Protease for Respiratory Parainfluenza Viruses", J. Virol., 87 (21):11930-11935.
Kabat et al. (1977) "Unusual Distributions of Amino Acids in Complementarity Determining (Hypervariable) Segments of Heavy and Light Chains of Immunoglobulins and Their Possible Roles in Specificity of Antibody-Combining Sites", J. Biol. Chem., 252:6609-6616.
Kabat et al. (1991) "Sequences of Proteins of Immunological Interest", National Institutes of Health, Bethesda, Md.; 5th ed.; NIH Publ. No. 91-3242.
Morrison et al. (1984) "Chimeric Human Antibody Molecules: Mouse Antigen-Binding Domains with Human Constant Region Domains", Proc. Natl. Acad. Sci. USA, 81:6851-6855.
NCBI Accession No. NM_005656.3, 2018.
NCBI Accession No. NM_015775.2 , 2021.
Order et al. (1985) "Analysis, Results, And Future Prospective of The Therapeutic Use of Radiolabeled Antibody in Cancer Therapy", Monoclonal Antibodies for Cancer Detection and Therapy, (eds.), pp. 303-316.
Prabhu et al. (2009) "Prophylactic and Therapeutic Efficacy of a Chimeric Monoclonal Antibody Specific for H5 Haemagglutinin Against Lethal H5N1 Influenza" Antivir Ther, 14(7):911-21.
Reineke (2004) "Antibody Epitope Mapping Using Arrays of Synthetic Peptides", Methods Mol. Biol., 248: 443-63.
Reinke et al. (2017) "Different Residues in the SARS-COV Spike Protein Determine Cleavage and Activation by the Host Cell Protease TMPRSS2", PLoS ONE, 12(6): e0179177.
Shen et al. (2017) "TMPRSS2: A Potential Target for Treatment of Influenza Virus and Coronavirus Infections", Biochimie, 142: 1-10.
Shirato et al. (2017) "Clinical Isolates of Human Coronavirus 229E Bypass the Endosome for Cell Entry", Journal of Virology, 91, e01387-16.
Shirogane et al. (2008) "Efficient Multiplication of Human Metapneumorvirus in Vero Cells Expressing the Transmembrane Serine Protease TMPRSS2", J. Virol., 82(17):8942-8946.
Studier & Moffatt (1986) Use of Bacteriophage T7 RNA Polymerase to Direct Selective High-Level Expression of Cloned Genes, J. Mol. Biol., 189(1): 113-30.
Tarnow et al. (2014) "TMPRSS2 is a Host Factor That is Essential for Pneumotropism and Pathogenicity of H7N9 Influenza A virus in Mice," Journal of Virology, 88(9):4744-4751.
Tomer (2000) "Characterization of a Discontinuous Epitope of the Human Immunodeficiency Virus (HIV) Core Protein P24 by Epitope Excision and Differential Chemical Modification Followed by Mass Spectrometric Peptide Mapping Analysis", Prot. Sci., 9: 487-496.
Ye et al. (2012) "Passive Immune Neutralization Strategies for Prevention and Control of Influenza A Infections", Immunotherapy, 4(2): 175-186.
Zeng et al. (2007) "Highly Pathogenic Avian Influenza H5N1 Viruses Elicit an Attenuated Type I Interferon Response In Polarized Human Bronchial Epithelial Cells", J Virol., 81:12439-12449.
Zhou et al. (2015) "Protease Inhibitors Targeting Coronavirus and Filovirus Entry", Antiviral Research, 116: 76-84.
Zmora et al. (2015) "TMPRSS2 Isoform 1 Activates Respiratory Viruses and Is Expressed in Viral Target Cells", PLoS ONE, 10(9):e0138380.
Zmora et al. (2017) "Non-Human Primate Orthologues of TMPRSS2 Cleave and Activate the Influenza Virus Hemagglutinin", PLoS ONE., 12:e0176597.
Kabat (1978) "The Structural Basis for Antibody Complementary", Adv. Prot. Chem., 32:1-75.
Thorpe et al. (1982) "The Preparation and Cytotoxic Properties of Antibody-Toxin Conjugates", Immunol. Rev., 62: 119-58.
Brown et al. (1996) "Tolerance to Single, but Not Multiple, Amino Acid Replacements in Antibody VHCDR2: A Means of Minimizing B Cell Wastage from Somatic Hypermutation?" Journal of Immunology, 156: 3285-3291.

\* cited by examiner

SEQUENCE LISTING

<160> NUMBER OF SEQ ID NOS: 64

<210> SEQ ID NO 1
<211> LENGTH: 357
<212> TYPE: DNA
<213> ORGANISM: Artificial Sequence
<220> FEATURE:
<223> OTHER INFORMATION: Synthetic -continued

<400> SEQUENCE: 1

```
gaggtgcagc tggtggagtc tggggaggc ttggtacagc ctggggggtc cctgagactc      60
tcctgtgaag cctctggatt caccttcagg agctacgaca tgcactgggt ccgccaagct    120
acaggaaaag gtctggagtg gtctcagct attggttctg ctggtgacac actctatcca    180
gactccgtga agggccgatt caccatctcc agagagaatg ccaagaactc cttgtatctt    240
caaatggaca gcctgagagc cggggacacg gctgtgtatt actgtgcaag agttggagac    300
tggggatcgg ggtacttaga ctactgggc cagggaaccc tggtcaccgt ctcctca       357
```

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Arg Ser Tyr
            20                  25                  30

Asp Met His Trp Val Arg Gln Ala Thr Gly Lys Gly Leu Glu Trp Val
        35                  40                  45

Ser Ala Ile Gly Ser Ala Gly Asp Thr Leu Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asp Ser Leu Arg Ala Gly Asp Thr Ala Val Tyr Tyr Cys Ala
                85                  90                  95

Arg Val Gly Asp Trp Gly Ser Gly Tyr Leu Asp Tyr Trp Gly Gln Gly
            100                 105                 110

Thr Leu Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct tcaggagcta cgac                                            24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Arg Ser Tyr Asp
1               5

<210> SEQ ID NO 5
<211> LENGTH: 21
<212> TYPE: DNA
<213> ORGANISM: Artificial Sequence
<220> FEATURE:

<223> OTHER INFORMATION: Synthetic

<400> SEQUENCE: 5
attggttctg ctggtgacac a    21

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Gly Ser Ala Gly Asp Thr
1               5

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gcaagagttg gagactgggg atcggggtac ttagactac    39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Ala Arg Val Gly Asp Trp Gly Ser Gly Tyr Leu Asp Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc ctgtctgcat ctgtaggaga cagagtcacc    60
atcacttgcc gggcaagtca gagcattagc atctatttaa attggtatca gcagaaacca    120
gggagagccc ctaaactcct gatctatgtt gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacggta ccccattcac tttcggccct    300
gggaccaaag tggatatcaa a    321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ile Tyr
            20                  25                  30

Leu Asn Trp Tyr Gln Gln Lys Pro Gly Arg Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Thr Pro Phe
                85                  90                  95

Thr Phe Gly Pro Gly Thr Lys Val Asp Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatta gcatctat                                              18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Ser Ile Ser Ile Tyr
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gttgcatcc                                                         9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Val Ala Ser
1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagagtt acggtacccc attcact                                    27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Gly Thr Pro Phe Thr
1               5

<210> SEQ ID NO 17
<211> LENGTH: 1341
<212> TYPE: DNA
<213> ORGANISM: Artificial Sequence
<220> FEATURE:
<223> OTHER INFORMATION: Synthetic

<400> SEQUENCE: 17

```
gaggtgcagc tggtggagtc tgggggaggc ttggtacagc ctggggggtc cctgagactc      60
tcctgtgaag cctctggatt caccttcagg agctacgaca tgcactgggt ccgccaagct     120
acaggaaaag gtctggagtg ggtctcagct attggttctg ctggtgacac actctatcca     180
gactccgtga agggccgatt caccatctcc agagagaatg ccaagaactc cttgtatctt     240
caaatggaca gcctgagagc cggggacacg gctgtgtatt actgtgcaag agttggagac     300
tggggatcgg ggtacttaga ctactggggc cagggaaccc tggtcaccgt ctcctcagcc     360
tccaccaagg gcccatcggt cttccccctg gcgccctgct ccaggagcac ctccgagagc     420
acagccgccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac gaagacctac     600
acctgcaacg tagatcacaa gcccagcaac accaaggtgg acaagagagt tgagtccaaa     660
tatggtcccc catgcccacc ctgcccagca cctgagttcc tggggggacc atcagtcttc     720
ctgttccccc caaaacccaa ggacactctc atgatctccc ggaccectga ggtcacgtgc     780 gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc tcccgtgct ggactccgac    1200 ggctccttct cctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                             1341
```

<210> SEQ ID NO 18
<211> LENGTH: 446
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Arg Ser Tyr
            20                  25                  30

Asp Met His Trp Val Arg Gln Ala Thr Gly Lys Gly Leu Glu Trp Val
        35                  40                  45

Ser Ala Ile Gly Ser Ala Gly Asp Thr Leu Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asp Ser Leu Arg Ala Gly Asp Thr Ala Val Tyr Tyr Cys Ala
                85                  90                  95

Arg Val Gly Asp Trp Gly Ser Gly Tyr Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415
```

```
Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 19
<211> LENGTH: 645
<212> TYPE: DNA
<213> ORGANISM: Artificial Sequence
<220> FEATURE:
<223> OTHER INFORMATION: Synthetic

<400> SEQUENCE: 19

```
gacatccaga tgacccagtc tccatcctcc ctgtctgcat ctgtaggaga cagagtcacc      60
atcacttgcc gggcaagtca gagcattagc atctatttaa attggtatca gcagaaacca     120
gggagagccc ctaaactcct gatctatgtt gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacggta cccccattca ctttcggccct     300
gggaccaaag tggatatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                      645
```

<210> SEQ ID NO 20
<211> LENGTH: 214
<212> TYPE: PRT
<213> ORGANISM: Artificial Sequence
<220> FEATURE:
<223> OTHER INFORMATION: Synthetic

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu Asn Trp Tyr Gln Gln Lys Pro Gly Arg Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Thr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

Ser Thr Leu Thr Leu Ser Lys Ala Asp Tyr Glu Lys His Lys Val Tyr
            165                 170                 175

Ala Cys Glu Val Thr His Gln Gly Leu Ser Ser Pro Val Thr Lys Ser
        180                 185                 190

Phe Asn Arg Gly Glu Cys
    195                 200                 205

210

<210> SEQ ID NO 21
<211> LENGTH: 351
<212> TYPE: DNA
<213> ORGANISM: Artificial Sequence
<220> FEATURE:
<223> OTHER INFORMATION: Synthetic

<400> SEQUENCE: 21
caggttcagc tggtgcagtc tggagctgag gtgaagaagc ctggggcctc agtgagggtc     60
tcctgcaagg cttctggtta cacctttacc aattatggta tcacctgggt gcgacaggcc    120
cctggacaag gcttgagtg gatgggaggg atcagcgttt acaatggtaa cacagaatat    180
gcagagaaat tccagggcag agtctccatg accacagaca catccacgac cacagcctac    240
ttggagctga ggagcctgaa atctgacgac acggccgtct atttctgtgc gagagggcaa    300
ctggactact cgaccctg gggccaggga accctggtca ctgtctcctc a    351

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Gly Ile Ser Val Tyr Asn Gly Asn Thr Glu Tyr Ala Glu Lys Phe
    50                  55                  60

Gln Gly Arg Val Ser Met Thr Thr Asp Thr Ser Thr Thr Thr Ala Tyr
65                  70                  75                  80

Leu Glu Leu Arg Ser Leu Lys Ser Asp Asp Thr Ala Val Tyr Phe Cys
                85                  90                  95

Ala Arg Gly Gln Leu Asp Tyr Phe Asp Pro Trp Gly Gln Gly Thr Leu
            100                 105                 110

Val Thr Val Ser Ser
        115

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
ggttacacct ttaccaatta tggt    24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Gly Tyr Thr Phe Thr Asn Tyr Gly
1               5

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
atcagcgttt acaatggtaa caca                                          24

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Ile Ser Val Tyr Asn Gly Asn Thr
1               5

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27
gcgagagggc aactggacta cttcgacccc                                    30

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Ala Arg Gly Gln Leu Asp Tyr Phe Asp Pro
1               5                   10

<210> SEQ ID NO 29
<211> LENGTH: 318
<212> TYPE: DNA
<213> ORGANISM: Artificial Sequence
<220> FEATURE:
<223> OTHER INFORMATION: Synthetic

<400> SEQUENCE: 29
gaaattgtga tgacgcagtc tccagccacc ctgtctgtgt ctccaggaga aagagccacc    60
ctctcctgca gggccagtca gagtgttaga agcaacttag cctggtacca gcagaaacct   120
ggccaggctc ccagtctcct catctatggt gcatccacca gggccactgg tatcccagcc   180
aggttcagtg gcagtgggtc tgggacagag ttcactctca ccatcagcag cctgcagtct    240
gaagattttg cagtttattt ctgtctgcag tataataact ggtggacgtt cggccaaggg    300
accaaggtgg aaatcaaa                                                  318

<210> SEQ ID NO 30
<211> LENGTH: 106
<212> TYPE: PRT
<213> ORGANISM: Artificial Sequence
<220> FEATURE:
<223> OTHER INFORMATION: Synthetic

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Ser Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Leu Gln Tyr Asn Asn Trp Trp Thr
                85                  90                  95

Phe Gly Gln Gly Thr Lys Val Glu Ile Lys
            100                 105

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31
cagagtgtta gaagcaac                                                   18

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Gln Ser Val Arg Ser Asn
1               5

<210> SEQ ID NO 33
<211> LENGTH: 9
<212> TYPE: DNA
<213> ORGANISM: Artificial Sequence
<220> FEATURE:
<223> OTHER INFORMATION: Synthetic

<400> SEQUENCE: 33 ggtgcatcc                                                              9

<210> SEQ ID NO 34
<211> LENGTH: 3
<212> TYPE: PRT
<213> ORGANISM: Artificial Sequence

```
<220> FEATURE:
<223> OTHER INFORMATION: Synthetic

<400> SEQUENCE: 34

Gly Ala Ser
1

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ctgcagtata ataactggtg gacg                                              24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Leu Gln Tyr Asn Asn Trp Trp Thr
1               5

<210> SEQ ID NO 37
<211> LENGTH: 1335
<212> TYPE: DNA
<213> ORGANISM: Artificial Sequence
<220> FEATURE:
<223> OTHER INFORMATION: Synthetic

<400> SEQUENCE: 37
caggttcagc tggtgcagtc tggagctgag gtgaagaagc ctggggcctc agtgagggtc        60
tcctgcaagg cttctggtta cacctttacc aattatggta tcacctgggt gcgacaggcc       120
cctggacaag gcttgagtg gatgggaggg atcagcgttt acaatggtaa cacagaatat       180
gcagagaaat tccagggcag agtctccatg accacagaca catccacgac acagcctac        240 ttggagctga ggagcctgaa atctgacgac acggccgtct atttctgtgc gagagggcaa       300
ctggactact cgaccctg gggccaggga accctggtca ctgtctcctc agcctccacc        360
aagggcccat cggtcttccc cctggcgccc tgctccagga gcacctccga gagcacagcc       420
gccctgggct gcctggtcaa ggactacttc cccgaaccgg tgacggtgtc gtggaactca       480
ggcgccctga ccagcggcgt gcacaccttc ccggctgtcc tacagtcctc aggactctac       540
tccctcagca gcgtggtgac cgtgccctcc agcagcttgg gcacgaagac ctacacctgc       600
aacgtagatc acaagcccag caacaccaag gtggacaaga gagttgagtc caaatatggt       660
cccccatgcc caccctgccc agcacctgag ttcctggggg gaccatcagt cttcctgttc       720 ccccccaaaac ccaaggacac tctcatgatc tcccggaccc ctgaggtcac gtgcgtggtg       780
gtggacgtga gccaggaaga ccccgaggtc cagttcaact ggtacgtgga tggcgtggag       840
gtgcataatg ccaagacaaa gccgcgggag gagcagttca acagcacgta ccgtgtggtc       900
agcgtcctca ccgtcctgca ccaggactgg ctgaacggca aggagtacaa gtgcaaggtc       960
tccaacaaag gctcccgtc ctccatcgag aaaaccatct ccaaagccaa agggcagccc       1020
cgagagccac aggtgtacac cctgccccca tcccaggagg agatgaccaa gaaccaggtc      1080
```

-continued

```
agcctgacct gcctggtcaa aggcttctac cccagcgaca tcgccgtgga gtgggagagc      1140
aatgggcagc cggagaacaa ctacaagacc acgcctcccg tgctggactc cgacggctcc      1200
ttcttcctct acagcaggct caccgtggac aagagcaggt ggcaggaggg gaatgtcttc      1260
tcatgctccg tgatgcatga ggctctgcac aaccactaca cacagaagtc cctctccctg      1320
tctctgggta aatga                                                       1335
```

<210> SEQ ID NO 38
<211> LENGTH: 444
<212> TYPE: PRT
<213> ORGANISM: Artificial Sequence
<220> FEATURE:
<223> OTHER INFORMATION: Synthetic

<400> SEQUENCE: 38

```
Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Gly Ile Ser Val Tyr Asn Gly Asn Thr Glu Tyr Ala Glu Lys Phe
    50                  55                  60

Gln Gly Arg Val Ser Met Thr Thr Asp Thr Ser Thr Thr Thr Ala Tyr
65                  70                  75                  80

Leu Glu Leu Arg Ser Leu Lys Ser Asp Asp Thr Ala Val Tyr Phe Cys
                85                  90                  95

Ala Arg Gly Gln Leu Asp Tyr Phe Asp Pro Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 39
<211> LENGTH: 642
<212> TYPE: DNA
<213> ORGANISM: Artificial Sequence
<220> FEATURE:
<223> OTHER INFORMATION: Synthetic

<400> SEQUENCE: 39
gaaattgtga tgacgcagtc tccagccacc ctgtctgtgt ctccaggaga aagagccacc      60
ctctcctgca gggccagtca gagtgttaga agcaacttag cctggtacca gcagaaacct     120
ggccaggctc ccagtctcct catctatggt gcatccacca gggccactgg tatcccagcc     180
aggttcagtg gcagtgggtc tgggacagag ttcactctca ccatcagcag cctgcagtct     240
gaagattttg cagtttattt ctgtctgcag tataataact ggtggacgtt cggccaaggg     300
accaaggtgg aaatcaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag      480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                         642

<210> SEQ ID NO 40
<211> LENGTH: 213
<212> TYPE: PRT
<213> ORGANISM: Artificial Sequence
<220> FEATURE:
<223> OTHER INFORMATION: Synthetic

<400> SEQUENCE: 40

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Ser Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
 65                  70                  75                  80

Glu Asp Phe Ala Val Tyr Phe Cys Leu Gln Tyr Asn Asn Trp Trp Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 363
<212> TYPE: DNA
<213> ORGANISM: Artificial Sequence
<220> FEATURE:
<223> OTHER INFORMATION: Synthetic

<400> SEQUENCE: 41
cagctgcagc tgcaggagtc gggcccagga ctggtgaagc cttcggagac cctgtccctc      60
acctgcactg tctctggtgg ctccatcaac agtaatagtt actactgggg ctggatccgc     120
cagcccccag ggaagggact ggagtggatt gggagtatct attatgatag aaacacctac     180
tacaccccgt ccctcaagag tcgagtcacc atatccgtag acacgtccaa gaaccagttc     240
tccctgaagc tgacctctgt gaccgccgca gacacggctg tatattattg tgcgagagag     300
caggtccccg gctactacgg tatggacgtc tggggccaag gaccacggt caccgtctcc     360 tca                                                                  363

<210> SEQ ID NO 42
<211> LENGTH: 121
<212> TYPE: PRT
<213> ORGANISM: Artificial Sequence
<220> FEATURE:
<223> OTHER INFORMATION: Synthetic

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Asn
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Asp Arg Asn Thr Tyr Tyr Thr Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
            85                  90                  95

Cys Ala Arg Glu Gln Val Pro Gly Tyr Tyr Gly Met Asp Val Trp Gly
            100                 105                 110

Gln Gly Thr Thr Val Thr Val Ser Ser
        115                 120

<210> SEQ ID NO 43
<211> LENGTH: 30
<212> TYPE: DNA
<213> ORGANISM: Artificial Sequence
<220> FEATURE:
<223> OTHER INFORMATION: Synthetic

<400> SEQUENCE: 43
ggtggctcca tcaacagtaa tagttactac                                    30

<210> SEQ ID NO 44
<211> LENGTH: 10
<212> TYPE: PRT
<213> ORGANISM: Artificial Sequence
<220> FEATURE:
<223> OTHER INFORMATION: Synthetic

<400> SEQUENCE: 44

Gly Gly Ser Ile Asn Ser Asn Ser Tyr Tyr
1               5                   10

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
atctattatg ataggaacac c                                             21

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Ile Tyr Tyr Asp Arg Asn Thr
1               5

<210> SEQ ID NO 47
<211> LENGTH: 39
<212> TYPE: DNA
<213> ORGANISM: Artificial Sequence
<220> FEATURE:
<223> OTHER INFORMATION: Synthetic

<400> SEQUENCE: 47
gcgagagagc aggtccccgg ctactacggt atggacgtc                          39

<210> SEQ ID NO 48
<211> LENGTH: 13
<212> TYPE: PRT
<213> ORGANISM: Artificial Sequence
<220> FEATURE:
<223> OTHER INFORMATION: Synthetic -continued

<400> SEQUENCE: 48

Ala Arg Glu Gln Val Pro Gly Tyr Tyr Gly Met Asp Val
1               5                   10

<210> SEQ ID NO 49
<211> LENGTH: 321
<212> TYPE: DNA
<213> ORGANISM: Artificial Sequence
<220> FEATURE:
<223> OTHER INFORMATION: Synthetic

<400> SEQUENCE: 49
gacatccagt tgacccagtc tccatccttc ctgtctgcat ctgtgggaga cagagtcacc      60
atcacttgct gggccagtca gggcattagc agatatttag cctggtatca gcaaaaacca     120
gggaaaaccc ctaaactcct gatctatgct gcatccactt tgcaaagtgg ggtcccatca     180
aggttcagcg gcactggatc tgggacagat ttcactctca caatcagcaa cctgcagcct     240
gaagattttg caacttatta ctgtcaacag tttgatagtt acccgtggac gttcggccaa     300
gggaccaagg tggaaatcaa a                                               321

<210> SEQ ID NO 50
<211> LENGTH: 107
<212> TYPE: PRT
<213> ORGANISM: Artificial Sequence
<220> FEATURE:
<223> OTHER INFORMATION: Synthetic

<400> SEQUENCE: 50

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Arg Tyr
            20                  25                  30

Leu Ala Trp Tyr Gln Gln Lys Pro Gly Lys Thr Pro Lys Leu Leu Ile
        35                  40                  45

Tyr Ala Ala Ser Thr Leu Gln Ser Gly Val Pro Ser Arg Phe Ser Gly
    50                  55                  60

Thr Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Phe Asp Ser Tyr Pro Trp
                85                  90                  95

Thr Phe Gly Gln Gly Thr Lys Val Glu Ile Lys
            100                 105

<210> SEQ ID NO 51
<211> LENGTH: 18
<212> TYPE: DNA
<213> ORGANISM: Artificial Sequence
<220> FEATURE:
<223> OTHER INFORMATION: Synthetic

<400> SEQUENCE: 51
cagggcatta gcagatat                                                    18

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

Gln Gly Ile Ser Arg Tyr
1               5

<210> SEQ ID NO 53
<211> LENGTH: 9
<212> TYPE: DNA
<213> ORGANISM: Artificial Sequence
<220> FEATURE:
<223> OTHER INFORMATION: Synthetic

<400> SEQUENCE: 53 gctgcatcc                                                                 9

<210> SEQ ID NO 54
<211> LENGTH: 3
<212> TYPE: PRT
<213> ORGANISM: Artificial Sequence
<220> FEATURE:
<223> OTHER INFORMATION: Synthetic

<400> SEQUENCE: 54

Ala Ala Ser
1

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
caacagtttg atagttaccc gtggacg                                            27

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Gln Gln Phe Asp Ser Tyr Pro Trp Thr
1               5

<210> SEQ ID NO 57
<211> LENGTH: 1347
<212> TYPE: DNA
<213> ORGANISM: Artificial Sequence
<220> FEATURE:
<223> OTHER INFORMATION: Synthetic

<400> SEQUENCE: 57
cagctgcagc tgcaggagtc gggcccagga ctggtgaagc cttcggagac cctgtccctc        60
acctgcactg tctctggtgg ctccatcaac agtaatagtt actactgggg ctggatccgc       120
cagcccccag ggaagggact ggagtggatt gggagtatct attatgatag gaacacctac       180
tacaccccgt ccctcaagag tcgagtcacc atatccgtag acacgtccaa gaaccagttc       240
tccctgaagc tgacctctgt gaccgccgca gacacggctg tatattattg tgcgagagag       300
caggtccccg gctactacgg tatggacgtc tggggccaag ggaccacggt caccgtctcc       360
tcagcctcca ccaagggccc atcggtcttc cccctggcgc cctgctccag gagcacctcc       420
gagagcacag ccgccctggg ctgcctggtc aaggactact ccccgaacc ggtgacggtg       480

```
tcgtggaact caggcgccct gaccagcggc gtgcacacct tcccggctgt cctacagtcc    540
tcaggactct actccctcag cagcgtggtg accgtgccct ccagcagctt gggcacgaag    600
acctacacct gcaacgtaga tcacaagccc agcaacacca aggtggacaa gagagttgag    660
tccaaatatg gtcccccatg cccaccctgc ccagcacctg agttcctggg ggaccatca    720 gtcttcctgt tccccccaaa acccaaggac actctcatga tctcccggac ccctgaggtc    780
acgtgcgtgg tggtggacgt gagccaggaa gaccccgagg tccagttcaa ctggtacgtg    840
gatggcgtgg aggtgcataa tgccaagaca aagccgcggg aggagcagtt caacagcacg    900
taccgtgtgg tcagcgtcct caccgtcctg caccaggact ggctgaacgg caaggagtac    960
aagtgcaagg tctccaacaa aggcctcccg tcctccatcg agaaaaccat ctccaaagcc   1020
aaagggcagc cccgagagcc acaggtgtac accctgcccc catcccagga ggagatgacc   1080
aagaaccagg tcagcctgac ctgcctggtc aaaggcttct accccagcga catcgccgtg   1140
gagtgggaga gcaatgggca gccggagaac aactacaaga ccacgcctcc cgtgctggac   1200
tccgacggct ccttcttcct ctacagcagg ctcaccgtgg acaagagcag gtggcaggag   1260
gggaatgtct tctcatgctc cgtgatgcat gaggctctgc acaaccacta cacacagaag   1320
tccctctccc tgtctctggg taaatga                                        1347
```

<210> SEQ ID NO 58
<211> LENGTH: 448
<212> TYPE: PRT
<213> ORGANISM: Artificial Sequence
<220> FEATURE:
<223> OTHER INFORMATION: Synthetic

<400> SEQUENCE: 58

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Asn
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Asp Arg Asn Thr Tyr Tyr Thr Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Glu Gln Val Pro Gly Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205
```

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 59
<211> LENGTH: 645
<212> TYPE: DNA
<213> ORGANISM: Artificial Sequence
<220> FEATURE:
<223> OTHER INFORMATION: Synthetic

<400> SEQUENCE: 59
gacatccagt tgacccagtc tccatccttc ctgtctgcat ctgtgggaga cagagtcacc        60
atcacttgct gggccagtca gggcattagc agatatttag cctggtatca gcaaaaacca       120
gggaaaaccc ctaaactcct gatctatgct gcatccactt tgcaaagtgg ggtcccatca       180
aggttcagcg gcactggatc tgggacagat ttcactctca caatcagcaa cctgcagcct       240
gaagattttg caacttatta ctgtcaacag tttgatagtt acccgtggac gttcggccaa       300
gggaccaagg tggaaatcaa acgaactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gttag                       645

```
<210> SEQ ID NO 60
<211> LENGTH: 214
<212> TYPE: PRT
<213> ORGANISM: Artificial Sequence
<220> FEATURE:
<223> OTHER INFORMATION: Synthetic

<400> SEQUENCE: 60

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Arg Tyr
            20                  25                  30

Leu Ala Trp Tyr Gln Gln Lys Pro Gly Lys Thr Pro Lys Leu Leu Ile
        35                  40                  45

Tyr Ala Ala Ser Thr Leu Gln Ser Gly Val Pro Ser Arg Phe Ser Gly
    50                  55                  60

Thr Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Phe Asp Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 1273
<212> TYPE: PRT
<213> ORGANISM: Artificial Sequence
<220> FEATURE:
<223> OTHER INFORMATION: Synthetic

<400> SEQUENCE: 61

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

```
Lys Ser Asn Ile Ile Arg Gly Trp Ile Phe Gly Thr Thr Leu Asp Ser
            100                 105                 110

Lys Thr Gln Ser Leu Leu Ile Val Asn Ala Thr Asn Val Val Ile
        115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
```

```
            515                 520                 525
Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
                610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
    930                 935                 940
```

```
Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 62
<211> LENGTH: 5
<212> TYPE: PRT
<213> ORGANISM: Artificial Sequence
<220> FEATURE:
<223> OTHER INFORMATION: Synthetic

<400> SEQUENCE: 62

Gly Gly Gly Gly Ser
1               5
```

<210> SEQ ID NO 63
<211> LENGTH: 492
<212> TYPE: PRT
<213> ORGANISM: Artificial Sequence
<220> FEATURE:
<223> OTHER INFORMATION: Synthetic

<400> SEQUENCE: 63

```
Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
            115                 120                 125

Pro Ser Asn Trp Cys Asp Gly Val Ser His Cys Pro Gly Gly Glu Asp
        130                 135                 140

Glu Asn Arg Cys Val Arg Leu Tyr Gly Pro Asn Phe Ile Leu Gln Met
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
            195                 200                 205

Phe Met Lys Leu Asn Thr Ser Ala Gly Asn Val Asp Ile Tyr Lys Lys
        210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
            275                 280                 285

Glu Trp Ile Val Thr Ala Ala His Cys Val Glu Lys Pro Leu Asn Asn
        290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365
```

-continued

```
Pro Gly Met Met Leu Gln Pro Glu Gln Leu Cys Trp Ile Ser Gly Trp
    370                 375                 380
Gly Ala Thr Glu Glu Lys Gly Lys Thr Ser Glu Val Leu Asn Ala Ala
385                 390                 395                 400
Lys Val Leu Leu Ile Glu Thr Gln Arg Cys Asn Ser Arg Tyr Val Tyr
                405                 410                 415
Asp Asn Leu Ile Thr Pro Ala Met Ile Cys Ala Gly Phe Leu Gln Gly
                420                 425                 430
Asn Val Asp Ser Cys Gln Gly Asp Ser Gly Gly Pro Leu Val Thr Ser
                435                 440                 445
Lys Asn Asn Ile Trp Trp Leu Ile Gly Asp Thr Ser Trp Gly Ser Gly
450                 455                 460
Cys Ala Lys Ala Tyr Arg Pro Gly Val Tyr Gly Asn Val Met Val Phe
465                 470                 475                 480
Thr Asp Trp Ile Tyr Arg Gln Met Arg Ala Asp Gly
                485                 490

<210> SEQ ID NO 64
<211> LENGTH: 492
<212> TYPE: PRT
<213> ORGANISM: Artificial Sequence
<220> FEATURE:
<223> OTHER INFORMATION: Synthetic

<400> SEQUENCE: 64

Met Ala Leu Asn Ser Gly Ser Pro Pro Gly Val Gly Pro Tyr Tyr Glu
1               5                   10                  15
Asn His Gly Tyr Gln Pro Glu Asn Pro Tyr Pro Ala Gln Pro Thr Val
                20                  25                  30
Ala Pro Asn Val Tyr Glu Val His Pro Ala Gln Tyr Tyr Pro Ser Pro
                35                  40                  45
Val Pro Gln Tyr Thr Pro Arg Val Leu Thr His Ala Ser Asn Pro Ala
50                  55                  60
Val Cys Arg Gln Pro Lys Ser Pro Ser Gly Thr Val Cys Thr Ser Lys
65                  70                  75                  80
Thr Lys Lys Ala Leu Cys Val Thr Met Thr Leu Gly Ala Val Leu Val
                85                  90                  95
Gly Ala Ala Leu Ala Ala Gly Leu Leu Trp Lys Phe Met Gly Ser Lys
                100                 105                 110
Cys Ser Asp Ser Gly Ile Glu Cys Asp Ser Ser Gly Thr Cys Ile Ser
                115                 120                 125
Leu Ser Asn Trp Cys Asp Gly Val Ser His Cys Pro Asn Gly Glu Asp
                130                 135                 140
Glu Asn Arg Cys Val Arg Leu Tyr Gly Pro Asn Phe Ile Leu Gln Val
145                 150                 155                 160
Tyr Ser Ser Gln Arg Lys Ser Trp His Pro Val Cys Arg Asp Asp Trp
                165                 170                 175
Asn Glu Asn Tyr Ala Arg Ala Ala Cys Arg Asp Met Gly Tyr Lys Asn
                180                 185                 190
Ser Phe Tyr Ser Ser Gln Gly Ile Val Asp Asn Ser Gly Ala Thr Ser
                195                 200                 205
Phe Met Lys Leu Asn Thr Ser Ala Gly Asn Val Asp Ile Tyr Lys Lys
                210                 215                 220
Leu Tyr His Ser Asp Ala Cys Ser Ser Lys Ala Val Val Ser Leu Arg
225                 230                 235                 240
```

```
Cys Ile Ala Cys Gly Val Arg Ser Asn Leu Ser Arg Gln Ser Arg Ile
            245                 250                 255

Val Gly Gly Gln Asn Ala Leu Leu Gly Ala Trp Pro Trp Gln Val Ser
            260                 265                 270

Leu His Val Gln Asn Ile His Val Cys Gly Gly Ser Ile Ile Thr Pro
        275                 280                 285

Glu Trp Ile Val Thr Ala Ala His Cys Val Glu Lys Pro Leu Asn Ser
    290                 295                 300

Pro Trp Gln Trp Thr Ala Phe Val Gly Thr Leu Arg Gln Ser Ser Met
305                 310                 315                 320

Phe Tyr Glu Lys Gly His Arg Val Glu Lys Val Ile Ser His Pro Asn
            325                 330                 335

Tyr Asp Ser Lys Thr Lys Asn Asn Asp Ile Ala Leu Met Lys Leu His
            340                 345                 350

Thr Pro Leu Thr Phe Asn Glu Val Val Lys Pro Val Cys Leu Pro Asn
            355                 360                 365

Pro Gly Met Met Leu Glu Pro Glu Gln His Cys Trp Ile Ser Gly Trp
    370                 375                 380

Gly Ala Thr Gln Glu Lys Gly Lys Thr Ser Asp Val Leu Asn Ala Ala
385                 390                 395                 400

Met Val Pro Leu Ile Glu Pro Arg Arg Cys Asn Asn Lys Tyr Val Tyr
            405                 410                 415

Asp Gly Leu Ile Thr Pro Ala Met Ile Cys Ala Gly Phe Leu Gln Gly
            420                 425                 430

Thr Val Asp Ser Cys Gln Gly Asp Ser Gly Gly Pro Leu Val Thr Leu
            435                 440                 445

Lys Asn Asp Val Trp Trp Leu Ile Gly Asp Thr Ser Trp Gly Ser Gly
            450                 455                 460

Cys Ala Gln Ala Asn Arg Pro Gly Val Tyr Gly Asn Val Thr Val Phe
465                 470                 475                 480

Thr Asp Trp Ile Tyr Arg Gln Met Arg Ala Asp Gly
                485                 490
```

ANTI-TMPRSS2 ANTIBODIES AND ANTIGEN-BINDING FRAGMENTS

RELATED APPLICATIONS

This application claims priority under 35 U.S.C. 119 (e) to U.S. Provisional Patent Application Ser. No. 62/972,338, filed Feb. 10, 2020; U.S. Provisional Patent Application Ser. No. 63/021,016, filed May 6, 2020; and U.S. Provisional Patent Application Ser. No. 63/094,199, filed Oct. 20, 2020, the disclosure of which are hereby incorporated by reference in their entirety.

GOVERNMENT LICENSE RIGHTS

This invention was made with Government support under Agreement HHSO100201700020C, awarded by the U.S. Department of Health and Human Services. The Government has certain rights in the invention.

SEQUENCE LISTING

An official copy of the sequence listing is submitted concurrently with the specification electronically via EFS-Web as an ASCII formatted sequence listing with a file name of "10737US01_Sequence_Listing_ST25.txt", a creation date of Feb. 9, 2021, and a size of about 64 KB. The sequence listing contained in this ASCII formatted document is part of the specification and is herein incorporated by reference in its entirety.

FIELD OF THE INVENTION

The present invention relates to antibodies and antigen-binding fragments that bind specifically to TMPRSS2 and methods for treating or preventing viral infections with said antibodies and fragments.

BACKGROUND OF THE INVENTION

Viruses such as influenza virus have acquired resistance to currently used drugs that target the viral neuraminidase (NA) or the ion channel protein, matrix protein 2 (M2). Moreover, newly identified viruses (such as coronaviruses) can be difficult to treat because they are not sufficiently characterized. The emergence of drug resistance and newly identified viruses highlights the need for the development of novel antiviral strategies. Host cell targeting may reduce or avoid the emergence of escape mutants, but could create a "sink" due to widespread expression and raise the concern for toxicity. A number of respiratory virus fusion proteins have been shown to require cleavage by host protease(s) for activation (Shirato et al. Clinical Isolates of Human Coronavirus 229E Bypass the Endosome for Cell Entry. Journal of Virology. 91, e01387-16 (2017); Reinke et al., Different residues in the SARS-CoV spike protein determine cleavage and activation by the host cell protease TMPRSS2. PLoS ONE. 12, e0179177 (2017); Zhou et al., Protease inhibitors targeting coronavirus and filovirus entry. Antiviral Research. 116, 76-84 (2015); Zmora et al. TMPRSS2 Isoform 1 Activates Respiratory Viruses and Is Expressed in Viral Target Cells. PLoS ONE. 10, e0138380 (2015)), including influenza (Zmora et al., Non-human primate orthologues of TMPRSS2 cleave and activate the influenza virus hemagglutinin. PLoS ONE. 12, e0176597 (2017); Böttcher-Friebertshäuser et al., Inhibition of influenza virus infection in human airway cell cultures by an antisense peptide-conjugated morpholino oligomer targeting the hemagglutinin-activating protease TMPRSS2. Journal of Virology. 85, 1554-1562 (2011); Bertram et al., TMPRSS2 and TMPRSS4 facilitate trypsin-independent spread of influenza virus in Caco-2 cells. Journal of Virology. 84, 10016-10025 (2010); Tarnow et al., TMPRSS2 is a host factor that is essential for pneumotropism and pathogenicity of H7N9 influenza A virus in mice. Journal of Virology (2014), May; 88(9):4744-51) and coronavirus (Heurich et al., TMPRSS2 and ADAM17 cleave ACE2 differentially and only proteolysis by TMPRSS2 augments entry driven by the severe acute respiratory syndrome coronavirus spike protein. Journal of Virology. 88, 2202-2013 (2014)).

Influenza A hemagglutinin precursor (HA0) requires cleavage by a host serine protease, to HA1 and HA2, for activation. For example, transmembrane protease, serine 2; TMPRSS2, TMPRSS4 and TMPRSS11D as well as human airway trypsin-like protease (HAT) have been implicated in HA cleavage (Bertram et al., TMPRSS2 and TMPRSS4 facilitate trypsin-independent spread of influenza virus in Caco-2 cells. Journal of Virology. 84, 10016-10025 (2010); Bottcher et al., Proteolytic Activation of Influenza Viruses by Serine Proteases TMPRSS2 and HAT from Human Airway Epithelium. Journal of Virology. 2006 Oct; 80(19): 9896-8; International patent application publication no. WO2017/151453). TMPRSS2 also cleaves and activates the spike protein in coronaviruses such as the severe acute respiratory syndrome coronavirus (SARS-CoV) (Heurich et al., TMPRSS2 and ADAM17 cleave ACE2 differentially and only proteolysis by TMPRSS2 augments entry driven by the severe acute respiratory syndrome coronavirus spike protein. Journal of Virology. 88, 2202-2013 (2014)). Additionally, TMPRSS2 is a target for anti-cancer therapy. See e.g., WO2008127347 and WO2002004953. A fusion between TMPRSS2 and ERG (TMPRSS2:ERG) is a gene fusion known to be a major driver of prostate carcinogenesis which is triggered by the ERα and repressed by the ERβ. Bonkhoff, Estrogen receptor signaling in prostate cancer: Implications for carcinogenesis and tumor progression, Prostate 78(1): 2-10 (2018).

SUMMARY OF THE INVENTION

Although there are small molecule inhibitors of TMPRSS2 and research antibodies, useful, for example, for immunohistochemistry, there is a need in the art for neutralizing therapeutic anti-TMPRSS2 antibodies and their use for treating or preventing viral infection. See e.g., Shen et al. Biochimie 142: 1-10 (2017), WO2008127347; WO2002004953; U.S. Pat. No. 9,498,529; antibody ab92323, available from Abcam (Cambridge, Mass.) or antibodies sc-515727 and sc-101847 available from Santa Cruz Biotech (Dallas, Tex.). The present invention addresses this need, in part, by providing human anti-human TMPRSS2 antibodies, such as mAb8021, mAb8029, and mAb8028, and combinations thereof including, for example, combinations with other therapeutics such as anti-influenza HA antibodies (e.g., Group I HA or Group II HA) or anti-coronavirus spike protein antibodies (e.g., Severe Acute Respiratory Syndrome (SARS) coronavirus (SARS-CoV), Middle East Respiratory Syndrome (MERS) coronavirus (MERS-CoV), and SARS-CoV-2 (the coronavirus responsible for COVID-19, previously referred to as 2019-nCoV)), and methods of use thereof for treating viral infections.

The present invention provides neutralizing human antigen-binding proteins that specifically bind to human TMPRSS2, for example, antibodies or antigen-binding fragments thereof. In some aspects, the antibody or antigen-binding fragment thereof is an isolated recombinant antibody or antigen-binding fragment thereof. In some embodiments, an antigen-binding protein comprises: (a) the CDR-H1, CDR-H2, and CDR-H3 of an immunoglobulin heavy chain that comprises the amino acid sequence set forth in SEQ ID NO: 2, 22, or 42; and/or (b) the CDR-L1, CDR-L2, and CDR-L3 of an immunoglobulin light chain that comprises the amino acid sequence set forth in SEQ ID NO: 10, 30, or 50. In an embodiment of the invention, an antigen-binding protein comprises: (a) a light chain immunoglobulin variable region comprising an amino acid sequence having at least 90% amino acid sequence identity to the amino acid sequence set forth in SEQ ID NO: 10, 30, or 50; and/or (b) a heavy chain immunoglobulin variable region comprising an amino acid sequence having at least 90% amino acid sequence identity to the amino acid sequence set forth in SEQ ID NO: 2, 22, or 42. In an embodiment of the invention, the present invention provides antigen-binding protein comprising: (a) CDR-L1, CDR-L2 and CDR-L3 of a light chain immunoglobulin comprising an amino acid sequence set forth in SEQ ID NO: 10, 30, or 50 and at least 90% amino acid sequence identity to the amino acid sequence set forth in SEQ ID NO: 10, 30, or 50; and/or (b) CDR-H1, CDR-H2 and CDR-H3 of a heavy chain immunoglobulin comprising an amino acid sequence set forth in SEQ ID NO: 2, 22, or 42 and at least 90% amino acid sequence identity to the amino acid sequence set forth in SEQ ID NO: 2, 22, or 42. For example, in an embodiment of the invention, the antigen-binding protein comprises a heavy chain immunoglobulin variable region that comprises (a) a CDR-H1 comprising the amino acid sequence: F T F R S Y D (SEQ ID NO: 4); (b) a CDR-H2 comprising the amino acid sequence: G S A G D T (SEQ ID NO: 6); (c) a CDR-H3 comprising the amino acid sequence: R V G D W G S G Y L D Y (SEQ ID NO: 8); and a light chain immunoglobulin variable region that comprises (a) a CDR-L1 comprising the amino acid sequence: S I S I Y (SEQ ID NO: 12); (b) a CDR-L2 comprising the amino acid sequence: A S (SEQ ID NO: 14); and/or (c) a CDR-L3 comprising the amino acid sequence: Q S Y G T P F T (SEQ ID NO: 16). The present invention also provides an antigen-binding protein comprising: (a) a heavy chain immunoglobulin that comprises the amino acid sequence set forth in SEQ ID NO: 18, 38, or 58; and/or (b) a light chain immunoglobulin that comprises the amino acid sequence set forth in SEQ ID NO: 20, 40, or 60.

In some aspects, the antigen-binding protein, e.g., the isolated recombinant antibody or antigen-binding fragment thereof, that specifically binds to human transmembrane protease, serine 2 (TMPRSS2), has one or more of the following characteristics:
(a) binds to TMPRSS2 with an $EC_{50}$ of less than about $10^{-9}$ M;
(b) demonstrates an increase in survival in a coronavirus-infected animal after administration to said coronavirus-infected animal, as compared to a comparable coronavirus-infected animal without said administration; and/or
(c) comprises
(i) three heavy chain complementarity determining regions (CDRs) (CDR-H1, CDR-H2, and CDR-H3) contained within a heavy chain variable region (HCVR) comprising an amino acid sequence having at least about 90% sequence identity to the HCVR set forth in SEQ ID NO: 2; and three light chain CDRs (CDR-L1, CDR-L2, and CDR-L3) contained within a light chain variable region (LCVR) comprising an amino acid sequence having at least about 90% sequence identity to the LCVR set forth in SEQ ID NO: 10; or
(ii) three heavy chain CDRs (CDR-H1, CDR-H2, and CDR-H3) contained within an HCVR comprising an amino acid sequence having at least about 90% sequence identity to the HCVR set forth in SEQ ID NO: 22; and three light chain CDRs (CDR-L1, CDR-L2, and CDR-L3) contained within an LCVR comprising an amino acid sequence having at least about 90% sequence identity to the LCVR set forth in SEQ ID NO: 30; or (iii) three heavy chain CDRs (CDR-H1, CDR-H2, and CDR-H3) contained within an HCVR comprising an amino acid sequence having at least about 90% sequence identity to the HCVR set forth in SEQ ID NO: 42; and three light chain CDRs (CDR-L1, CDR-L2, and CDR-L3) contained within an LCVR comprising an amino acid sequence having at least about 90% sequence identity to the LCVR set forth in SEQ ID NO: 50.

In some aspects, the antigen-binding protein, e.g., the antibody or antigen-binding fragment thereof, comprises the three heavy chain CDRs (CDR-H1, CDR-H2, and CDR-H3) contained within the HCVR comprising an amino acid sequence having at least about 90% sequence identity to the HCVR set forth in SEQ ID NO: 2; and the three light chain CDRs (CDR-L1, CDR-L2, and CDR-L3) contained within the LCVR comprising an amino acid sequence having at least about 90% sequence identity to the LCVR set forth in SEQ ID NO: 10.

In some aspects, the antigen-binding protein, e.g., the antibody or antigen-binding fragment thereof, comprises: (a) an immunoglobulin heavy chain variable region comprising the CDR-H1, CDR-H2, and CDR-H3 of an immunoglobulin heavy chain that comprises the amino acid sequence set forth in SEQ ID NO: 2; and/or (b) an immunoglobulin light chain variable region comprising the CDR-L1, CDR-L2, and CDR-L3 of an immunoglobulin light chain that comprises the amino acid sequence set forth in SEQ ID NO: 10.

In some aspects, the antigen-binding protein, e.g., the antibody or antigen-binding fragment thereof, comprises: (a) a heavy chain immunoglobulin variable region comprising an amino acid sequence having at least 90% amino acid sequence identity to the amino acid sequence set forth in SEQ ID NO: 2; and/or (b) a light chain immunoglobulin variable region comprising an amino acid sequence having at least 90% amino acid sequence identity to the amino acid sequence set forth in SEQ ID NO: 10.

In some aspects, the antigen-binding protein, e.g., the antibody or antigen-binding fragment thereof, comprises: a heavy chain immunoglobulin variable region that comprises
(a) a CDR-H1 comprising the amino acid sequence of SEQ ID NO: 4,
(b) a CDR-H2 comprising the amino acid sequence of SEQ ID NO: 6, and/or
(c) a CDR-H3 comprising the amino acid sequence of SEQ ID NO: 8; and/or
a light chain immunoglobulin variable region that comprises
(a) a CDR-L1 comprising the amino acid sequence of SEQ ID NO: 12,
(b) a CDR-L2 comprising the amino acid sequence of SEQ ID NO: 14, and/or
(c) a CDR-L3 comprising the amino acid sequence of SEQ ID NO: 16.

In some aspects, the antigen-binding protein, e.g., the antibody or antigen-binding fragment thereof, comprises: (a) a heavy chain immunoglobulin that comprises the amino acid sequence set forth in SEQ ID NO: 18, or an immunoglobulin heavy chain variable region that comprises the amino acid sequence set forth in SEQ ID NO: 2; and/or (b) a light chain immunoglobulin that comprises the amino acid sequence set forth in SEQ ID NO: 20, or an immunoglobulin light chain variable region that comprises the amino acid sequence set forth in SEQ ID NO: 10.

In some aspects, the antigen-binding protein, e.g., the antibody or antigen-binding fragment thereof, comprises the three heavy chain CDRs (CDR-H1, CDR-H2, and CDR-H3) contained within the HCVR comprising an amino acid sequence having at least about 90% sequence identity to the HCVR set forth in SEQ ID NO: 22; and the three light chain CDRs (CDR-L1, CDR-L2, and CDR-L3) contained within the LCVR comprising an amino acid sequence having at least about 90% sequence identity to the LCVR set forth in SEQ ID NO: 30.

In some aspects, the antigen-binding protein, e.g., the antibody or antigen-binding fragment thereof, comprises (a) an immunoglobulin heavy chain variable region comprising the CDR-H1, CDR-H2, and CDR-H3 of an immunoglobulin heavy chain that comprises the amino acid sequence set forth in SEQ ID NO: 22; and/or (b) an immunoglobulin light chain variable region comprising the CDR-L1, CDR-L2, and CDR-L3 of an immunoglobulin light chain that comprises the amino acid sequence set forth in SEQ ID NO: 30.

In some aspects, the antigen-binding protein, e.g., the antibody or antigen-binding fragment thereof, comprises (a) a heavy chain immunoglobulin variable region comprising an amino acid sequence having at least 90% amino acid sequence identity to the amino acid sequence set forth in SEQ ID NO: 22; and/or (b) a light chain immunoglobulin variable region comprising an amino acid sequence having at least 90% amino acid sequence identity to the amino acid sequence set forth in SEQ ID NO: 30.

In some aspects, the antigen-binding protein, e.g., the antibody or antigen-binding fragment thereof, comprises: a heavy chain immunoglobulin variable region that comprises
    (a) a CDR-H1 comprising the amino acid sequence of SEQ ID NO: 24,
    (b) a CDR-H2 comprising the amino acid sequence of SEQ ID NO: 26, and/or
    (c) a CDR-H3 comprising the amino acid sequence of SEQ ID NO: 28; and/or
    a light chain immunoglobulin variable region that comprises
    (a) a CDR-L1 comprising the amino acid sequence of SEQ ID NO: 32,
    (b) a CDR-L2 comprising the amino acid sequence of SEQ ID NO: 34, and/or
    (c) a CDR-L3 comprising the amino acid sequence of SEQ ID NO: 36.

In some aspects, the antigen-binding protein, e.g., the antibody or antigen-binding fragment thereof, comprises: (a) a heavy chain immunoglobulin that comprises the amino acid sequence set forth in SEQ ID NO: 38, or an immunoglobulin heavy chain variable region that comprises the amino acid sequence set forth in SEQ ID NO: 22; and/or (b) a light chain immunoglobulin that comprises the amino acid sequence set forth in SEQ ID NO: 40, or an immunoglobulin light chain variable region that comprises the amino acid sequence set forth in SEQ ID NO: 30.

In some aspects, the antigen-binding protein, e.g., the antibody or antigen-binding fragment thereof, comprises: the three heavy chain CDRs (CDR-H1, CDR-H2, and CDR-H3) contained within the HCVR comprising an amino acid sequence having at least about 90% sequence identity to the HCVR set forth in SEQ ID NO: 42; and the three light chain CDRs (CDR-L1, CDR-L2, and CDR-L3) contained within the LCVR comprising an amino acid sequence having at least about 90% sequence identity to the LCVR set forth in SEQ ID NO: 50.

In some aspects, the antigen-binding protein, e.g., the antibody or antigen-binding fragment thereof, comprises: (a) an immunoglobulin heavy chain variable region comprising the CDR-H1, CDR-H2, and CDR-H3 of an immunoglobulin heavy chain that comprises the amino acid sequence set forth in SEQ ID NO: 42; and/or (b) an immunoglobulin light chain variable region comprising the CDR-L1, CDR-L2, and CDR-L3 of an immunoglobulin light chain that comprises the amino acid sequence set forth in SEQ ID NO: 50.

In some aspects, the antigen-binding protein, e.g., the antibody or antigen-binding fragment thereof, comprises: (a) a heavy chain immunoglobulin variable region comprising an amino acid sequence having at least 90% amino acid sequence identity to the amino acid sequence set forth in SEQ ID NO: 42; and/or (b) a light chain immunoglobulin variable region comprising an amino acid sequence having at least 90% amino acid sequence identity to the amino acid sequence set forth in SEQ ID NO: 50.

In some aspects, the antigen-binding protein, e.g., the antibody or antigen-binding fragment thereof, comprises:
    (a) a CDR-H1 comprising the amino acid sequence of SEQ ID NO: 44,
    (b) a CDR-H2 comprising the amino acid sequence of SEQ ID NO: 46, and/or
    (c) a CDR-H3 comprising the amino acid sequence of SEQ ID NO: 48; and/or
    a light chain immunoglobulin variable region that comprises
    (a) a CDR-L1 comprising the amino acid sequence of SEQ ID NO: 52,
    (b) a CDR-L2 comprising the amino acid sequence of SEQ ID NO: 54, and/or
    (c) a CDR-L3 comprising the amino acid sequence of SEQ ID NO: 56.

In some aspects, the antigen-binding protein, e.g., the antibody or antigen-binding fragment thereof, comprises: (a) a heavy chain immunoglobulin that comprises the amino acid sequence set forth in SEQ ID NO: 58, or an immunoglobulin heavy chain variable region that comprises the amino acid sequence set forth in SEQ ID NO: 42; and/or (b) a light chain immunoglobulin that comprises the amino acid sequence set forth in SEQ ID NO: 60, or an immunoglobulin light chain variable region that comprises the amino acid sequence set forth in SEQ ID NO: 50.

The present invention also provides any anti-TMPRSS2 antigen-binding protein that competes with any antigen-binding protein that is set forth herein for binding to TMPRSS2 (e.g., as determined by use of using a real time, label-free bio-layer interferometry assay, e.g., on an Octet RED384 biosensor (Pall ForteBio Corp.)); or which binds to the same or an overlapping epitope on TMPRSS2 (or a fragment thereof) as any antigen-binding protein that is set forth herein.

The present invention also provides multispecific antigen-binding proteins that bind to TMPRSS2 and another antigen or to TMPRSS2 at a different epitope. For example, the multispecific molecule comprises (a) a first antigen-binding domain that binds specifically to TMPRSS2; and (b) a second antigen-binding domain that binds specifically to another antigen or to TMPRSS2 or to an epitope which differs from that of the first antigen-binding domain. In some aspects, the multispecific antigen-binding protein is an antibody or antigen-binding fragment thereof.

The present invention also provides any anti-TMPRSS2 antigen-binding protein (e.g., an antibody or antigen-binding fragment, e.g., comprising a sequence set forth herein) that comprises one or more of the following properties:
   Inhibits growth of influenza virus (e.g., A/Puerto Rico/08/1934 (H1N1)) or coronavirus (e.g., SARS-CoV, MERS-CoV, or SARS-CoV-2) in TMPRSS2-expressing cells (e.g., Calu-3 cells);
   Binds to the surface of TMPRSS-expressing cells;
   Does not significantly bind to MDCK/Tet-on cells which do not express TMPRSS2;
   Limits spread of influenza virus infection or coronavirus infection of cells in vitro; and/or
   Protects a mouse engineered to express the human TMPRSS2 protein from death and/or weight loss caused by influenza virus infection or coronavirus infection.

The present invention also provides a complex comprising any antigen-binding protein set forth herein bound to a TMPRSS2 polypeptide, e.g., in vitro or in the body of a subject.

The present invention also provides a method for making an anti-TMPRSS2 antigen-binding protein set forth herein (e.g., mAb8021, mAb8028, or mAb8029) or immunoglobulin chain thereof comprising: (a) introducing one or more polynucleotides encoding a light and/or a heavy immunoglobulin chain of the said antigen-binding protein; (b) culturing the host cell (e.g., CHO cell, *Pichia* cell or *Pichia pastoris* cell) under conditions favorable to expression of the polynucleotide; and (c) optionally, isolating the antigen-binding protein or immunoglobulin chain from the host cell and/or medium in which the host cell is grown. An antigen-binding protein or immunoglobulin chain which is a product of such a method is part of the present invention.

A polypeptide comprising: (a) CDR-H1, CDR-H2, and CDR-H3 of a $V_H$ domain of an antibody or antigen-binding fragment that comprises the amino acid sequence set forth in any one of SEQ ID NO: 2, 22, or 42; or (b) CDR-L1, CDR-L2, and CDR-L3 of a $V_L$ domain of an immunoglobulin chain that comprises the amino acid sequence set forth in SEQ ID NO: 10, 30, or 50, also forms part of the present invention. In some embodiments, provided herein is a polynucleotide encoding said polypeptide.

A polypeptide (e.g., an immunoglobulin) comprising: (a) CDR1, CDR2, and CDR3 of a $V_H$ domain of an immunoglobulin chain that comprises the amino acid sequence set forth in SEQ ID NO: 2; or (b) CDR1, CDR2, and CDR3 of a $V_L$ domain of an immunoglobulin chain that comprises the amino acid sequence set forth in SEQ ID NO: 10 (e.g., wherein the polypeptide is in a host cell) also forms part of the present invention. Similarly, the present invention provides a polypeptide comprising (a) CDR1, CDR2, and CDR3 of a $V_H$ domain of an immunoglobulin chain that comprises the amino acid sequence set forth in SEQ ID NO: 22; or (b) CDR1, CDR2, and CDR3 of a $V_L$ domain of an immunoglobulin chain that comprises the amino acid sequence set forth in SEQ ID NO: 30 (e.g., wherein the polypeptide is in a host cell). Similarly, the present invention provides a polypeptide comprising (a) CDR1, CDR2, and CDR3 of a $V_H$ domain of an immunoglobulin chain that comprises the amino acid sequence set forth in SEQ ID NO: 42; or (b) CDR1, CDR2, and CDR3 of a $V_L$ domain of an immunoglobulin chain that comprises the amino acid sequence set forth in SEQ ID NO: 50 (e.g., wherein the polypeptide is in a host cell). In some embodiments, provided herein is a polynucleotide encoding said polypeptide.

The present invention also provides a polynucleotide (e.g., DNA or RNA) that encoded a polypeptide of the present invention. In an embodiment of the invention, the polynucleotide encodes two different immunoglobulin chains (e.g., heavy and light). In an embodiment of the invention, one polynucleotide encodes a light immunoglobulin chain and another polynucleotide encodes a heavy immunoglobulin chain, e.g., wherein the chains are in a host cell or are in a vessel. For example, the polynucleotide is in a vector (e.g., a plasmid) and/or is integrated into a host cell chromosome.

The present invention also provides a vector comprising a polynucleotide as described herein.

Host cells (e.g., CHO cell, *Pichia* cell or *Pichia pastoris* cell) of the present invention may include an anti-TMPRSS2 antigen-binding protein (e.g., mAb8021, mAb8028, or mAb8029), polypeptide thereof or polynucleotide encoding such a polypeptide and/or a vector including such a polynucleotide.

The present invention also provides a composition or kit comprising an anti-TMPRSS2 antigen-binding protein set forth herein (e.g., mAb8021, mAb8028, or mAb8029) in association with a further therapeutic agent (e.g., an antiviral drug and/or a vaccine). For example, the composition may be a pharmaceutical composition comprising the antigen-binding protein and pharmaceutically acceptable carrier and, optionally, a further therapeutic agent. The further therapeutic agent may be remdesivir, chloroquine, lopinavir, ritonavir, ribavirin, ledipasvir, sofosbuvir, a combination of ledipasvir and sofosbuvir, oseltamivir, zanamivir, ribavirin and interferon-alpha2b, interferon-alpha2a and/or an antibody or antigen-binding fragment thereof that specifically binds to influenza HA or coronavirus spike protein. In an embodiment of the invention, the further therapeutic agent is an antibody or antigen binding fragment thereof selected from the group consisting of H1H14611N2; H1H14612N2; H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B;

H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18215B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; and H1H18335B, as set forth in International patent application publication no. WO2016/100807. In an embodiment of the invention, the further therapeutic agent is an antibody or antigen binding fragment thereof selected from the group consisting of H4sH15188P; H1H15188P; H1H15211P; H1H15177P; H4sH15211P; H1H15260P2; H1H15259P2; H1H15203P; H4sH15260P2; H4sH15231P2; H1H15237P2; H1H15208P; H1H15228P2; H1H15233P2; H1H15264P2; H1H15231P2; H1H15253P2; H1H15215P; and H1H15249P2, as set forth in International patent application publication no. WO/2015/179535.

In an embodiment of the invention, a further therapeutic agent which is provided in association with an anti-TMPRSS2 antigen-binding protein is an antibody or antigen-binding fragment that binds to influenza Group II HA protein, such as H1H14611N2; or an antibody or fragment that comprises $V_H$ and $V_L$ of H1H14611N2; or a heavy chain immunoglobulin comprising CDR-H1, CDR-H2 and CDR-H3 of H1H14611N2 and a light chain immunoglobulin comprising CDR-L1, CDR-L2 and CDR-L3 of H1H14611N2.

In an embodiment of the invention, a further therapeutic agent which is provided in association with an anti-TMPRSS2 antigen-binding protein is an antibody or antigen-binding fragment that binds to influenza Group II HA protein, such as H1H14612N2; or an antibody or fragment that comprises $V_H$ and $V_L$ of H1H14612N2; or a heavy chain immunoglobulin comprising CDR-H1, CDR-H2 and CDR-H3 of H1H14612N2 and a light chain immunoglobulin comprising CDR-L1, CDR-L2 and CDR-L3 of H1H14612N2.

In an embodiment of the invention, a further therapeutic agent which is provided in association with an anti-TMPRSS2 antigen-binding protein is an antibody or antigen-binding fragment that binds to influenza Group I HA protein, such as H1H11729P; or an antibody or fragment that comprises $V_H$ and $V_L$ of H1H11729P; or a heavy chain immunoglobulin comprising CDR-H1, CDR-H2 and CDR-H3 of H1H11729P and a light chain immunoglobulin comprising CDR-L1, CDR-L2 and CDR-L3 of H1H11729P.

The present invention also provides a vessel or injection device that comprises an anti-TMPRSS2 antigen-binding protein (e.g., mAb8021, mAb8028, or mAb8029) or composition thereof (e.g., pharmaceutical composition).

The present invention also provides a method for treating or preventing a viral infection other than an influenza virus infection, in a subject (e.g., a human) in need thereof, comprising administering a therapeutically effective amount of anti-TMPRSS2 antigen-binding protein set forth herein (e.g., mAb8021, mAb8028, or mAb8029).

The present invention also provides a method for treating or preventing cancer (e.g., prostate cancer, colon cancer, lung cancer, pancreas cancer, urinary tract cancer, breast cancer, ovarian cancer, prostate adenocarcinoma, renal cell carcinoma, colorectal adenocarcinoma, lung adenocarcinoma, lung squamous cell carcinoma, and/or pleural mesothelioma) or infection, e.g., a viral infection, e.g., an infection with an influenza virus, coronavirus, SARS-CoV, MERS-CoV, SARS-CoV-2, parainfluenza virus, human metapneumovirus or hepatitis C virus (HCV), in a subject (e.g., a human) in need thereof, comprising administering a therapeutically effective amount of anti-TMPRSS2 antigen-binding protein set forth herein (e.g., mAb8021, mAb8028, or mAb8029).

In some aspects, the method comprises administering the antigen-binding protein in association with one or more further therapeutic agents (e.g., anti-viral drug and/or a vaccine). In an embodiment of the invention, a further therapeutic agent is a member selected from the group consisting of: remdesivir, chloroquine, lopinavir, ritonavir, ribavirin, ledipasvir, sofosbuvir, a combination of ledipasvir and sofosbuvir, oseltamivir, zanamivir, ribavirin and interferon-alpha2b, interferon-alpha2a and an antibody or antigen-binding fragment thereof that specifically binds to influenza HA. In an embodiment of the invention, a further therapeutic agent is an antibody or antigen binding fragment thereof selected from the group consisting of H1H14611N2; H1H14612N2; H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; and H1H18335B, as set forth in International patent application publication no. WO2016/100807. In an embodiment of the invention, the further therapeutic agent is an antibody or antigen binding fragment thereof selected from the group consisting of H4sH15188P; H1H15188P; H1H15211P; H1H15177P; H4sH15211P; H1H15260P2; H1H15259P2; H1H15203P; H4sH15260P2; H4sH15231P2; H1H15237P2; H1H15208P; H1H15228P2; H1H15233P2; H1H15264P2; H1H15231P2; H1H15253P2; H1H15215P; and H1H15249P2, as set forth in International patent application publication no. WO/2015/179535.

The present invention also provides a method for administering an anti-TMRPSS2 antigen-binding protein (e.g., mAb8021, mAb8028, or mAb8029) set forth herein into the body of a subject (e.g., a human) comprising injecting the antigen-binding protein into the body of the subject. In some aspects, the antigen-binding protein is injected into the body of the subject parenterally (e.g., subcutaneously, intravenously or intramuscularly).

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "coronavirus" or "CoV" refers to any virus of the coronavirus family, including but not limited to MERS-CoV, SARS-CoV, and SARS-CoV-2. SARS-CoV-2 refers to the newly-emerged coronavirus that causes COVID-19, This virus was initially identified as the cause of a serious outbreak starting in Wuhan, China, and rapidly spread around the globe. It binds via the viral spike protein to human host cell receptor angiotensin-converting enzyme 2 (ACE2). The spike protein also binds to and is cleaved by TMPRSS2, which activates the spike protein for membrane fusion of the virus.

The term "CoV-S", also called "S protein" refers to the spike protein of a coronavirus, and can refer to specific S proteins such as MERS-CoV-S, SARS-CoV-S, and SARS-CoV-2-S. The SARS-CoV-2 spike protein is a 1273 amino acid type I membrane glycoprotein which assembles into trimers that constitute the spikes or peplomers on the surface of the enveloped coronavirus particle. The protein has two essential functions, host receptor binding and membrane fusion, which are attributed to the N-terminal (51) and C-terminal (S2) halves of the S protein. CoV-S binds to its cognate receptor via a receptor binding domain (RBD) present in the 51 subunit. The amino acid sequence of full-length SARS-CoV-2 spike protein is exemplified by the amino acid sequence provided in SEQ ID NO: 61. The term "CoV-S" includes protein variants of CoV spike protein isolated from different CoV isolates as well as recombinant CoV spike protein or a fragment thereof. The term also encompasses CoV spike protein or a fragment thereof coupled to, for example, a histidine tag, mouse or human Fc, or a signal sequence such as ROR1.

The term "coronavirus infection" or "CoV infection," as used herein, refers to infection with a coronavirus such as MERS-CoV, SARS-CoV, or SARS-CoV-2. The term includes respiratory tract infection, often in the lower respiratory tract. The symptoms include high fever, cough, shortness of breath pneumonia, gastro-intestinal symptoms such as diarrhea, organ failure (kidney failure and renal dysfunction), septic shock and death in severe cases. Infection with SARS-CoV-2 can cause Coronavirus Disease 19 (COVID-19), which may cause symptoms such as fever, chills, shortness of breath, congestion, cough, fatigue, body/muscle aches, and loss of taste and/or smell.

The term "influenza hemagglutinin", also called "influenza HA" is a trimeric glycoprotein found on the surface of influenza virions, which mediates viral attachment (via HA1 binding to α-2,3- and α-2,6-sialic acids) and entry (through conformational change) into host cells. The HA is comprised of two structural domains: a globular head domain containing the receptor binding site (subject to high frequency of antigenic mutations) and the stem region (more conserved among various strains of influenza virus). The influenza HA is synthesized as a precursor (HA0) that undergoes proteolytic processing to produce two subunits (HA1 and HA2) which associate with one another to form the stem/globular head structure. The viral HA is the most variable antigen on the virus and the stem (HA2) is highly conserved within each group.

The term "influenza neuraminidase", also called "influenza NA" is an exosialidase (EC 3.2.1.18) which cleaves α-ketosidic linkage between the sialic (N-acetylneuraminic) acid and an adjacent sugar residue.

The amino acid sequence of full-length Influenza HA is exemplified by the amino acid sequence of influenza isolate H1N1 A/California/04/2009 provided in GenBank as accession number FJ966082.1. The term "influenza-HA" also includes protein variants of influenza HA isolated from different influenza isolates, e.g., GQ149237.1, NC_002017, KM972981.1, etc. The term "influenza-HA" also includes recombinant influenza HA or a fragment thereof. The term also encompasses influenza HA or a fragment thereof coupled to, for example, histidine tag, mouse or human Fc, or a signal sequence.

An anti-TMPRSS2 "antigen-binding protein" is a polypeptide or complex of more than one polypeptide (e.g., a tetrameric IgG antibody) that binds specifically to TMPRSS2 polypeptide, for example, an anti-TMPRSS2 antibody or antigen-binding fragment whether monospecific or multispecific.

TMPRSS2

TMPRSS2 (Transmembrane protease serine 2) is a protein, located on human chromosome 21, that belongs to the serine protease family (type II transmembrane serine proteases (TTSPs)) which is important for influenza virus infectivity. TMPRSS2 has been demonstrated to mediate cleavage of influenza virus HA0 to HA1 and HA2.

The human TMPRSS2 gene encodes a predicted protein of 492 amino acids which anchors to the plasma membrane. The protein converts to its mature form through autocatalytic cleavage between Arg255 and Ile256. After cleavage, the mature proteases are mostly membrane bound, yet a portion of them may be liberated into the extracellular milieu.

In an embodiment of the invention, human TMPRSS2 (V160M) comprises the amino acid sequence:

(SEQ ID NO: 63; methionine 160 in bold font)
MALNSGSPPAIGPYYENHGYQPENPYPAQPTVVPTVYEVHPAQYYPSPVP

QYAPRVLTQASNPVVCTQPKSPSGTVCTSKTKKALCITLTLGTFLVGAAL

AAGLLWKFMGSKCSNSGIECDSSGTCINPSNWCDGVSHCPGGEDENRCVR

LYGPNFILQMYSSQRKSWHPVCQDDWNENYGRAACRDMGYKNNFYSSQGI

VDDSGSTSFMKLNTSAGNVDIYKKLYHSDACSSKAVVSLRCIACGVNLNS

SRQSRIVGGESALPGAWPWQVSLHVQNVHVCGGSIITPEWIVTAAHCVEK

-continued

```
PLNNPWHWTAFAGILRQSFMFYGAGYQVEKVISHPNYDSKTKNNDIALMK

LQKPLTFNDLVKPVCLPNPGMMLQPEQLCWISGWGATEEKGKTSEVLNAA

KVLLIETQRCNSRYVYDNLITPAMICAGFLQGNVDSCQGDSGGPLVTSKN

NIWWLIGDTSWGSGCAKAYRPGVYGNVMVFTDWIYRQMRADG.
```

In an embodiment of the invention, the TMPRSS2 polypeptide does not comprise the V160M mutation. See also NCBI Accession No. NM_005656.3.

In an embodiment of the invention, *Macaca mulatta* TMPRSS2 (S129L, N251S, I415V, R431Q, D492G) comprises the amino acid sequence:

```
                                              (SEQ ID NO: 64)
MALNSGSPPGVGPYYENHGYQPENPYPAQPTVAPNVYEVHPAQYYPSPVP

QYTPRVLTHASNPAVCRQPKPSGTVCTSKTKKALCVTMTLGAVLVGAAL

AAGLLWKFMGSKCSDSGIECDSSGTCISLSNWCDGVSHCPNGEDENRCVR

LYGPNFILQVYSSQRKSWHPVCRDDWNENYARAACRDMGYKNSFYSSQGI

VDNSGATSFMKLNTSAGNVDIYKKLYHSDACSSKAVVSLRCIACGVRSNL

SRQSRIVGGQNALLGAWPWQVSLHVQNIHVCGGSIITPEWIVTAAHCVEK

PLNSPWQWTAFVGTLRQSSMFYEKGHRVEKVISHPNYDSKTKNNDIALMK

LHTPLTFNEVVKPVCLPNPGMMLEPEQHCWISGWGATQEKGKTSDVLNAA

MVPLIEPRRCNNKYVYDGLITPAMICAGFLQGTVDSCQGDSGGPLVTLKN

DVWWLIGDTSWGSGCAQANRPGVYGNVTVFTDWIYRQMRADG.
```

In an embodiment of the invention, the TMPRSS2 polypeptide does not comprise the S129L, N251S, I415V, R431Q and/or D492G mutation.

In an embodiment of the invention, *Mus musculus* TMPRSS2 mRNA comprises the nucleotide sequence set forth in NCBI Accession No. NM_015775.2.

Viruses

The present invention includes methods for treating or preventing a viral infection in a subject. The term "virus" includes any virus whose infection in the body of a subject is treatable or preventable by administration of an anti-TMPRSS2 antibody or antigen-binding fragment thereof (e.g., wherein infectivity of the virus is at least partially dependent on TMPRSS2). In an embodiment of the invention, a "virus" is any virus that expresses HA0, spike protein (e.g., CoV-S), or another substrate of TMPRSS2 whose proteolytic cleavage is required for full infectivity of the virus against a cell in a host. The term "virus" also includes a TMPRSS2-dependent respiratory virus which is a virus that infects the respiratory tissue of a subject (e.g., upper and/or lower respiratory tract, trachea, bronchi, lungs) and is treatable or preventable by administration of an anti-TMPRSS2. For example, in an embodiment of the invention, virus includes influenza virus, coronavirus, SARS-CoV (severe acute respiratory syndrome coronavirus), MERS-CoV (Middle East Respiratory Syndrome (MERS) coronavirus), SARS-CoV-2, parainfluenza virus, Sendai virus (SeV), human metapneumovirus and/or hepatitis C virus (HCV). "Viral infection" refers to the invasion and multiplication of a virus in the body of a subject. The present invention includes embodiments with a proviso that "virus" excludes influenza virus, e.g., wherein viral infection excludes influenza virus infection.

Coronavirus virions are spherical with diameters of approximately 125 nm. The most prominent feature of coronaviruses is the club-shape spike projections emanating from the surface of the virion. These spikes are a defining feature of the virion and give them the appearance of a solar corona, prompting the name, coronaviruses. Within the envelope of the virion is the nucleocapsid. Coronaviruses have helically symmetrical nucleocapsids, which is uncommon among positive-sense RNA viruses, but far more common for negative-sense RNA viruses. MERS-CoV (Middle East Respiratory Syndrome coronavirus), SARS-CoV (severe acute respiratory syndrome coronavirus), and SARS-CoV-2 belong to the coronavirus family. The initial attachment of the virion to the host cell is initiated by interactions between the S protein and its receptor. The sites of receptor binding domains (RBD) within the S1 region of a coronavirus S protein vary depending on the virus, with some having the RBD at the C-terminus of 51. The S-protein/receptor interaction is the primary determinant for a coronavirus to infect a host species and also governs the tissue tropism of the virus. Many coronaviruses utilize peptidases as their cellular receptor. Following receptor binding, the virus must next gain access to the host cell cytosol. This is generally accomplished by acid-dependent proteolytic cleavage of S protein by a cathepsin, TMPRRS2 or another protease, followed by fusion of the viral and cellular membranes.

Influenza viruses are members of the family Orthomyxoviridae. This family represents enveloped viruses the genome of which has segmented negative-sense single-strand RNA segments. There are four genera of this family: types A, B, C and Thogotovirus. The Influenza viruses classes, A, B and C, are based on core protein and are further divided into subtypes determined by the viral envelope glycoproteins hemagglutinin (HA) and neuraminidase (NA) (e.g., subtype A/H1N1). There are at least 18 influenza hemagglutinin ("HA") protein subtypes (H1-H18 or HA1-HA18) and at least 11 influenza neuraminidase (NA) protein subtypes (N1-N11 or NA1-NA11) used to define influenza subtypes. Group 1 influenza has H1, H2, H5, H6, H8, H9, H11, H12, H13, H16, H17 and H18 subtypes and NAB, NA5, Na4 and NA1 subtypes. Group 2 has H3, H4, H7, H10, H14 and H15 subtypes and NA6, NA9, NA7, NA2 and NA3 subtypes. Influenza A viruses infect a range of mammalian and avian species, whereas type B and C infections are largely restricted to humans. The eight genome segments of influenza A and B viruses are loosely encapsidated by the nucleoprotein.

There are now two genera of human parainfluenza virus (HPIV), respirovirus (HPIV-1 and HPIV-3) and rubulavirus (HPIV-2 and HPIV-4). Both genera (paramyxoviruses) can be separated morphologically from influenza virus.

Sendai virus, also known as murine parainfluenza virus, is the type species in the genus respirovirus, which also contains the species human parainfluenza virus 3, bovine parainfluenza virus 3, and human parainfluenza virus 1. TMPRSS2 Is an Activating Protease for Respiratory Parainfluenza Viruses such as parainfluenza viruses and Sendai virus (SeV). See et al. Abe et al., J. Virol. 87(21): 11930-11935 (2013).

Human metapneumovirus (HMPV) is classified as the first human member of the Metapneumovirus genus in the Pneumovirinae subfamily within the Paramyxoviridae family. It is an enveloped negative-sense single-stranded RNA virus. The RNA genome includes 8 genes coding for 9 different proteins. HMPV is identical in gene order to the avian pneumovirus (AMPV), which also belongs to the Metapneumovirus genus. TMPRSS2 is expressed in the human lung epithelium, cleaves the HMPV F protein efficiently and supports HMPV multiplication and may be involved in the development of lower respiratory tract illness in HMPV-infected patients. See et al. Shirogane et al. J Virol. 82(17): 8942-8946 (2008).

Hepatitis C virus (HCV) is a small, enveloped, positive-sense single-stranded RNA virus of the family Flaviviridae. HCV, with at least 6 genotypes and numerous subtypes, is a member of the hepacivirus genus. TMPRSS2 may activate HCV infection at the post-binding and entry stage. Esumi et al., Hepatology 61(2): 437-446 (2015).

Anti-TMPRSS2 Antibodies and Antigen-Binding Fragments

The present invention provides antigen-binding proteins, such as antibodies and antigen-binding fragments thereof, that specifically bind to TMPRSS2 protein or an antigenic fragment thereof.

The term "antibody", as used herein, refers to immunoglobulin molecules comprising four polypeptide chains, two heavy chains (HCs) and two light chains (LCs) inter-connected by disulfide bonds (i.e., "full antibody molecules"), as well as multimers thereof (e.g. IgM). Exemplary antibodies include, for example, mAb8021, mAb8028, and mAb8029. Each heavy chain comprises a heavy chain variable region ("HCVR" or "$V_H$") (e.g., SEQ ID NO 2) and a heavy chain constant region (comprised of domains $C_H1$, $C_H2$ and $C_H3$). Each light chain is comprised of a light chain variable region ("LCVR" or "$V_L$") (e.g., SEQ ID NO 4) and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences, or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

The present invention includes monoclonal anti-TMPRSS2 antigen-binding proteins, e.g., antibodies and antigen-binding fragments thereof, as well as monoclonal compositions comprising a plurality of isolated monoclonal antigen-binding proteins. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-TMPRSS2 antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4) or IgM. In an embodiment of the invention, an antigen-binding protein, e.g., antibody or antigen-binding fragment comprises a light chain constant domain, e.g., of the type kappa or lambda.

The term "human" antigen-binding protein, such as an antibody, as used herein, includes antibodies having variable and constant regions derived from human germline immunoglobulin sequences whether in a human cell or grafted into a non-human cell, e.g., a mouse cell. See e.g., U.S. Pat. No. 8,502,018, 6,596,541 or 5,789,215. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject. See below.

The present invention includes anti-TMPRSS2 chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) Proc. Natl. Acad. Sci. USA 81: 6851-6855).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a cell (e.g., CHO cells) expression system or isolated from a recombinant combinatorial human antibody library.

Recombinant anti-TMPRSS2 antigen-binding proteins, e.g., antibodies and antigen-binding fragments, disclosed herein may also be produced in an E. coli/T7 expression system. In this embodiment, nucleic acids encoding the anti-TMPRSS2 antibody immunoglobulin molecules of the invention (e.g., mAb8021, mAb8028, or mAb8029) may be inserted into a pET-based plasmid and expressed in the E. coli/T7 system. For example, the present invention includes methods for expressing an antibody or antigen-binding fragment thereof or immunoglobulin chain thereof in a host cell (e.g., bacterial host cell such as E. coli such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as an *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952,496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Thus, the present invention includes recombinant methods for making an anti-TMPRSS2 antigen-binding protein, such as an antibody or antigen-binding fragment thereof of the present invention, or an immunoglobulin chain thereof, comprising (i) introducing one or more polynucleotides (e.g., including the nucleotide sequence in any one or more of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, or 59) encoding light and/or heavy immunoglobulin chains, or CDRs, of the antigen-binding protein, e.g., mAb8021, mAb8028, or mAb8029, for example, wherein the polynucleotide is in a vector; and/or integrated into a host cell chromosome and/or is operably linked to a promoter; (ii) culturing the host cell (e.g., CHO or *Pichia* or *Pichia pastoris*) under condition favorable to expression of the polynucleotide and, (iii) optionally, isolating the antigen-binding protein, (e.g., antibody or fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain. For example, the present invention also includes anti-TMPRSS2 antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 1 and a light chain immunoglobulin (or variable domain thereof or comprising the CDRs thereof) encoded by the nucleotide sequence set forth in SEQ ID NO: 9 which are the product of such production methods, and, optionally, the purification methods set forth herein. The present invention also includes anti-TMPRSS2 antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 21 and a light chain immunoglobulin (or variable domain thereof or comprising the CDRs thereof) encoded by the nucleotide sequence set forth in SEQ ID NO: 29 which are the product of such production methods, and, optionally, the purification methods set forth herein. The present invention also includes anti-TMPRSS2 antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 41 and a light chain immunoglobulin (or variable domain thereof or comprising the CDRs thereof) encoded by the nucleotide sequence set forth in SEQ ID NO: 49 which are the product of such production methods, and, optionally, the purification methods set forth herein. For example, in an embodiment of the invention, the product of the method is an anti-TMPRSS2 antigen-binding protein which is an antibody or fragment comprising a $V_H$ comprising the amino acid sequence set forth in SEQ ID NO: 2 and a $V_L$ comprising the amino acid sequence set forth in SEQ ID NO: 10; or comprising a HC comprising the amino acid sequence set forth in SEQ ID NO: 18 and a LC comprising the amino acid sequence set forth in SEQ ID NO: 20. In another embodiment of the invention, the product of the method is an anti-TMPRSS2 antigen-binding protein which is an antibody or fragment comprising a $V_H$ comprising the amino acid sequence set forth in SEQ ID NO: 22 and a $V_L$ comprising the amino acid sequence set forth in SEQ ID NO: 30; or comprising a HC comprising the amino acid sequence set forth in SEQ ID NO: 38 and a LC comprising the amino acid sequence set forth in SEQ ID NO: 40. In another embodiment of the invention, the product of the method is an anti-TMPRSS2 antigen-binding protein which is an antibody or fragment comprising a $V_H$ comprising the amino acid sequence set forth in SEQ ID NO: 42 and a $V_L$ comprising the amino acid sequence set forth in SEQ ID NO: 50; or comprising a HC comprising the amino acid sequence set forth in SEQ ID NO: 58 and a LC comprising the amino acid sequence set forth in SEQ ID NO: 60.

Eukaryotic and prokaryotic host cells, including mammalian cells, may be used as hosts for expression of an anti-TMPRSS2 antigen-binding protein. Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermo-* tolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens and Neurospora crassa. The present invention includes an isolated host cell (e.g., a CHO cell) comprising an antigen-binding protein, such as mAb8021, mAb8028, or mAb8029; or a polynucleotide encoding such a polypeptide thereof.

The term "specifically binds" refers to those antigen-binding proteins (e.g., mAbs) having a binding affinity to an antigen, such as TMPRSS2 protein (e.g., human TMPRSS2), expressed as $K_D$, of at least about $10^{-8}$ M (e.g., $2.81 \times 10^{-9}$M; $9.31 \times 10^{-9}$M; $10^{-9}$ M; $10^{-10}$M, $10^{-11}$ M, or $10^{-12}$ M), as measured by real-time, label free bio-layer interferometry assay, for example, at 25° C. or 37° C., e.g., an Octet® HTX biosensor, or by surface plasmon resonance, e.g., BIACORE™, or by solution-affinity ELISA. The present invention includes antigen-binding proteins that specifically bind to TMPRSS2 protein.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., as defined in WO08/020079 or WO09/138519) (e.g., monovalent nanobodies, bivalent nanobodies, etc.), small modular immunopharmaceuticals (SMIPs), and shark variable IgNAR domains, are also encompassed within the expression "antigen-binding fragment," as used herein. In an embodiment of the invention, the antigen-binding fragment comprises three or more CDRs of mAb8021, mAb8028, or mAb8029 (e.g., CDR-H1, CDR-H2 and CDR-H3; or CDR-L1, CDR-L2 and CDR-L3).

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

Antigen-binding proteins (e.g., antibodies and antigen-binding fragments) may be mono-specific or multi-specific (e.g., bi-specific). Multispecific antigen-binding proteins are discussed further herein.

In specific embodiments, antibody or antibody fragments of the invention may be conjugated to a moiety such a ligand or a therapeutic moiety ("immunoconjugate"), such as an anti-viral drug, a second anti-influenza antibody, or any other therapeutic moiety useful for treating a viral infection, e.g., influenza viral infection. See below.

The present invention also provides a complex comprising an anti-TMPRSS2 antigen-binding protein, e.g., antibody or antigen-binding fragment, discussed herein complexed with TMPRSS2 polypeptide or an antigenic fragment thereof and/or with a secondary antibody or antigen-binding fragment thereof (e.g., detectably labeled secondary antibody) that binds specifically to the anti-TMPRSS2 antibody or fragment. In an embodiment of the invention, the antibody or fragment is in vitro (e.g., is immobilized to a solid substrate) or is in the body of a subject. In an embodiment of the invention, the TMPRSS2 is in vitro (e.g., is immobilized to a solid substrate) or is on the surface of a cell or is in the body of a subject. Immobilized anti-TMRPSS2 antibodies and antigen-binding fragments thereof which are covalently linked to an insoluble matrix material (e.g., glass or polysaccharide such as agarose or sepharose, e.g., a bead or other particle thereof) are also part of the present invention; optionally, wherein the immobilized antibody is complexed with TMPRSS2 or antigenic fragment thereof or a secondary antibody or fragment thereof.

"Isolated" antigen-binding proteins, antibodies or antigen-binding fragments thereof, polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The term "epitope" refers to an antigenic determinant (e.g., on TMPRSS2 polypeptide) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) (e.g., coversin) interacts is hydrogen/deuterium exchange detected by mass spectrometry. In general terms, the hydrogen/deuterium exchange method involves deuterium-labeling the protein of interest, followed by binding the antigen-binding protein, e.g., antibody or fragment or polypeptide, to the deuterium-labeled protein. Next, the TMPRSS2 protein/antigen-binding protein complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein (e.g., antibody or fragment or polypeptide), the target protein is subjected to protease cleavage and mass spectrometry analysis, thereby revealing the deuterium-labeled residues which correspond to the specific amino acids with which the antigen-binding protein interacts. See, e.g., Ehring (1999) Analytical Biochemistry 267: 252-259; Engen and Smith (2001) Anal. Chem. 73: 256A-265A.

The term "competes" as used herein, refers to an antigen-binding protein (e.g., antibody or antigen-binding fragment thereof) that binds to an antigen (e.g., TMPRSS2) and inhibits or blocks the binding of another antigen-binding protein (e.g., antibody or antigen-binding fragment thereof) to the antigen. The term also includes competition between two antigen-binding proteins e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. In an embodiment of the invention, competition between a first and second anti-TMPRSS2 antigen-binding protein (e.g., antibody) is determined by measuring the ability of an immobilized first anti-TMPRSS2 antigen-binding protein (e.g., antibody) (not initially complexed with TMPRSS2 protein) to bind to soluble TMPRSS2 protein complexed with a second anti-TMPRSS2 antigen-binding protein (e.g., antibody). A reduction in the ability of the first anti-TMPRSS2 antigen-binding protein (e.g., antibody) to bind to the complexed TMPRSS2 protein, relative to uncomplexed TMPRSS2 protein, indicates that the first and second anti-TMPRSS2 antigen-binding proteins (e.g., antibodies) compete. The degree of competition can be expressed as a percentage of the reduction in binding. Such competition can be measured using a real time, label-free bio-layer interferometry assay, e.g., on an Octet RED384 biosensor (Pall ForteBio Corp.), ELISA (enzyme-linked immunosorbent assays) or SPR (surface plasmon resonance).

Binding competition between anti-TMPRSS2 antigen-binding proteins (e.g., monoclonal antibodies (mAbs)) can be determined using a real time, label-free bio-layer interferometry assay on an Octet RED384 biosensor (Pall ForteBio Corp.). For example, to determine competition between two anti-human TMPRSS2 monoclonal antibodies, the anti-TMPRSS2 mAb can be first captured onto anti-hFc antibody coated Octet biosensor tips (Pall ForteBio Corp., #18-5060) by submerging the tips into a solution of anti-human TMPRSS2 mAb (subsequently referred to as "mAb1"). As a positive-control for blocking, the antibody captured biosensor tips can then be saturated with a known blocking isotype control mAb (subsequently referred to as "blocking mAb") by dipping into a solution of blocking mAb. To determine if mAb2 competes with mAb1, the biosensor tips can then be subsequently dipped into a co-complexed solution of human TMPRSS2 polypeptide and a second anti-human TMPRSS2 mAb (subsequently referred to as "mAb2"), that had been pre-incubated for a period of time and binding of mAb1 to the TMPRSS2 polypeptide can be determined. The biosensor tips can be washed in buffer in between every step of the experiment. The real-time binding response can be monitored during the course of the experiment and the binding response at the end of every step can be recorded.

For example, in an embodiment of the invention, the competition assay is conducted at 25° C. and pH about 7, e.g., 7.4, e.g., in the presence of buffer, salt, surfactant and a non-specific protein (e.g., bovine serum albumin).

Typically, an antibody or antigen-binding fragment of the invention which is modified in some way retains the ability to specifically bind to TMPRSS2, e.g., retains at least 10% of its TMPRSS2 binding activity (when compared to the parental antibody) when that activity is expressed on a molar basis. Preferably, an antibody or antigen-binding fragment of the invention retains at least 20%, 50%, 70%, 80%, 90%, 95% or 100% or more of the TMPRSS2 binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., mAb8021 $V_H$, $V_L$, HC, or LC, mAb8028 $V_H$, $V_L$, HC, or LC, or mAb8029 $V_H$, $V_L$, HC, or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 10, 18, 20, 22, 30, 38, 40, 42, 50, 58, or 60); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., at least about 70, 72, 74, 75, 76, 79, 80, 81, 82, 83, 84, 85, 86, 87, 88, 89, 90, 91, 92, 93, 94, 95, 96, 97, 98, 99, 99.5, or 99.9%) identical to a referenced nucleotide sequence that is set forth herein (e.g., SEQ ID NO: 1, 9, 17, 19, 21, 29, 37, 39, 41, 49, 57, or 59); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

Anti-TMPRSS2 antigen-binding proteins, e.g., antibodies and antigen-binding fragments thereof of the present invention, in an embodiment of the invention, include a heavy chain immunoglobulin variable region having at least 70% (e.g., 80%, 85%, 90%, 95%, 99%) amino acid sequence identity to the amino acids set forth in SEQ ID NO: 2, 18, 22, 38, 42, or 58; and/or a light chain immunoglobulin variable region having at least 70% (e.g., 80%, 85%, 90%, 95%, 99%) amino acid sequence identity to the amino acids set forth in SEQ ID NO: 10, 20, 30, 40, 50, or 60.

In addition, a variant anti-TMPRSS2 antigen-binding protein may include a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), nonsense mutations, deletions, or insertions. For example, the present invention includes antigen-binding proteins which include an immunoglobulin light chain variant comprising the amino acid sequence set forth in SEQ ID NO: 10, 20, 30, 40, 50, or 60 but having one or more of such mutations and/or an immunoglobulin heavy chain variant comprising the amino acid sequence set forth in SEQ ID NO: 2, 18, 22, 38, 42, or 58 but having one or more of such mutations. In an embodiment of the invention, a variant anti-TMPRSS2 antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions).

The invention further provides variant anti-TMPRSS2 antigen-binding proteins, e.g., antibodies or antigen-binding fragments thereof, comprising one or more variant CDRs (e.g., any one or more of CDR-L1, CDR-L2, CDR-L3, CDR-H1, CDR-H2 and/or CDR-H3) that are set forth herein with at least 70%, 75%, 80%, 85%, 90%, 95%, 98%, 99% or 99.9% sequence identity or similarity to, e.g., SEQ ID NO: 4, 6, 8, 12, 14, and/or 16; or 24, 26, 28, 32, 34, and/or 36; or 44, 46, 48, 52, 54, and/or 56.

Embodiments of the present invention also include variant antigen-binding proteins, e.g., anti-TMPRSS2 antibodies and antigen-binding fragments thereof, that comprise immunoglobulin $V_H$s and $V_L$s; or HCs and LCs, which comprise an amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise the amino acid sequence set forth in SEQ ID NOs: 4, 6, 8, 12, 14, and 16; or 24, 26, 28, 32, 34, and 36; or 44, 46, 48, 52, 54, and 56, respectively. Thus, in such embodiments, the CDRs within variant antigen-binding proteins are not, themselves, variants.

Conservatively modified variant anti-TMPRSS2 antibodies and antigen-binding fragments thereof are also part of the present invention. A "conservatively modified variant" or a "conservative substitution" refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4$^{th}$ Ed.)). In addition, substitutions of structurally or functionally similar amino acids are less likely to significantly disrupt biological activity.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45.

Function-conservative variants of the anti-TMPRSS2 antibodies and antigen-binding fragments thereof are also part of the present invention. Any of the variants of the anti-TMPRSS2 antibodies and antigen-binding fragments thereof (as discussed herein) may be "function-conservative variants". Such function-conservative variants may, in some cases, also be characterized as conservatively modified variants. "Function-conservative variants," as used herein, refers to variants of the anti-TMPRSS2 antibodies or antigen-binding fragments thereof in which one or more amino acid residues have been changed without significantly altering one or more functional properties of the antibody or fragment. In an embodiment of the invention, a function-conservative variant anti-TMPRSS2 antibody or antigen-binding fragment thereof of the present invention comprises a variant amino acid sequence and exhibits one or more of the following functional properties:

Inhibits growth of influenza virus (e.g., A/Puerto Rico/ 08/1934 (H1N1)) or coronavirus (e.g., SARS-CoV-2) in TMPRSS2-expressing cells (e.g., Calu-3 cells);

Does not significantly bind to MDCK/Tet-on cells which do not express TMPRSS2;

Limits spread of coronavirus infection (e.g., by SARS-CoV-2) or influenza virus infection (e.g., by H1_PR34; H1_CA09; H1_Bris; H9N2 or H3N2 influenza virus) of cells, e.g., Calu-3, in vitro; and/or
- Protects a mouse engineered to express the human TMPRSS2 protein from death caused by influenza virus infection (e.g., H1N1, or H3N2) or coronavirus infection (e.g., SARS-CoV-2), for example, wherein the mice are infected with an otherwise lethal dose of the virus, optionally when combined with an anti-HA or an anti-spike protein antibody.
- Protects a mouse engineered to express the human TMPRSS2 protein from weight loss caused by influenza virus infection (e.g., H1N1, or H3N2) or coronavirus infection (e.g., SARS-CoV-2), for example, wherein the mice are infected with a dose of the virus that would otherwise cause weight loss, optionally when combined with an anti-HA or an anti-spike protein antibody.

The present invention includes a mouse engineered to express the human TMPRSS2 protein which includes, within the mouse's body, an anti-TMPRSS2 antigen-binding protein (e.g., antibody or antigen-binding fragment) such as mAb8021, mAb8028, or mAb8029. See International patent application publication no. WO2017/151453.

A "neutralizing" or "antagonist" anti-TMPRSS2 antigen-binding protein, e.g., antibody or antigen-binding fragment, refers to a molecule that inhibits an activity of TMPRSS2 to any detectable degree, e.g., inhibits protease activity of TMPRSS2, for example, of a substrate such as HA; Cbz-Gly-Gly-Arg-AMC (Sigma), where Cbz is benzyloxycarbonyl and AMC is 7-amino-4-methylcoumarin; influenza virus HA0; coronavirus S protein; or precursor TMPRSS2 which is autocatalytically cleaved between Arg255 and Ile256 and/or inhibits influenza virus entry into a cell and/or inhibits influenza virus reproduction in the body of a subject.

mAb8021, mAb8028, and mAb8029 refer to antigen-binding proteins, such as antibodies and antigen-binding fragments thereof, that comprise the heavy chain or $V_H$ (or a variant thereof) and light chain or $V_L$ (or a variant thereof) as set forth below; or that comprise a $V_H$ that comprises the CDRs thereof (CDR-H1 (or a variant thereof), CDR-H2 (or a variant thereof) and CDR-H3 (or a variant thereof)) and a $V_L$ that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below.

In an embodiment of the invention, mAb8028 refers to an antibody or antigen-binding fragment thereof comprising CDR-H1, CDR-H2, and CDR-H3 of an immunoglobulin heavy chain that comprises the amino acid sequence set forth in SEQ ID NO: 2 or 18 and CDR-L1, CDR-L2, and CDR-L3 of an immunoglobulin light chain that comprises the amino acid sequence set forth in SEQ ID NO: 10 or 20.

In an embodiment of the invention, mAb8021 refers to an antibody or antigen-binding fragment thereof comprising CDR-H1, CDR-H2, and CDR-H3 of an immunoglobulin heavy chain that comprises the amino acid sequence set forth in SEQ ID NO: 22 or 38 and CDR-L1, CDR-L2, and CDR-L3 of an immunoglobulin light chain that comprises the amino acid sequence set forth in SEQ ID NO: 30 or 40.

In an embodiment of the invention, mAb8029 refers to an antibody or antigen-binding fragment thereof comprising CDR-H1, CDR-H2, and CDR-H3 of an immunoglobulin heavy chain that comprises the amino acid sequence set forth in SEQ ID NO: 42 or 58 and CDR-L1, CDR-L2, and CDR-L3 of an immunoglobulin light chain that comprises the amino acid sequence set forth in SEQ ID NO: 50 or 60.

In an embodiment of the invention, mAb8028 refers to an antibody or antigen-binding fragment thereof comprising a $V_H$ that comprises the amino acid sequence set forth in SEQ ID NO: 2; and a $V_L$ that comprises the amino acid sequence set forth in SEQ ID NO: 10.

In an embodiment of the invention, mAb8021 refers to an antibody or antigen-binding fragment thereof comprising a $V_H$ that comprises the amino acid sequence set forth in SEQ ID NO: 22; and a $V_L$ that comprises the amino acid sequence set forth in SEQ ID NO: 30.

In an embodiment of the invention, mAb8029 refers to an antibody or antigen-binding fragment thereof comprising a $V_H$ that comprises the amino acid sequence set forth in SEQ ID NO: 42; and a $V_L$ that comprises the amino acid sequence set forth in SEQ ID NO: 50.

In an embodiment of the invention, mAb8028 refers to an antibody or antigen-binding fragment comprising a heavy chain immunoglobulin that comprises the amino acid sequence set forth in SEQ ID NO: 18; and a light chain immunoglobulin that comprises the amino acid sequence set forth in SEQ ID NO: 20.

In an embodiment of the invention, mAb8021 refers to an antibody or antigen-binding fragment comprising a heavy chain immunoglobulin that comprises the amino acid sequence set forth in SEQ ID NO: 38; and a light chain immunoglobulin that comprises the amino acid sequence set forth in SEQ ID NO: 40.

In an embodiment of the invention, mAb8029 refers to an antibody or antigen-binding fragment comprising a heavy chain immunoglobulin that comprises the amino acid sequence set forth in SEQ ID NO: 58; and a light chain immunoglobulin that comprises the amino acid sequence set forth in SEQ ID NO: 60.

The antibodies described herein also include embodiments wherein the $V_H$ is fused to a wild-type IgG4 (e.g., wherein residue 108 is S) or to IgG4 variants (e.g., wherein residue 108 is P).

Antibodies and antigen-binding fragments of the present invention comprise immunoglobulin chains including the amino acid sequences set forth herein as well as cellular and in vitro post-translational modifications to the antibody. For example, the present invention includes antibodies and antigen-binding fragments thereof that specifically bind to TMPRSS2 comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

Administration of Antibodies

The present invention provides methods for administering an anti-TMPRSS2 antigen-binding protein of the present invention, e.g., mAb8021, mAb8028, or mAb8029, comprising introducing the antigen-binding protein into the body of a subject (e.g., a human). For example, the method comprises piercing the body of the subject with a needle of a syringe and injecting the antigen-binding protein into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising an anti-TMPRSS2 antigen-binding protein of the present invention, e.g., mAb8021, mAb8028, or mAb8029.

The present invention also provides an injection device comprising one or more antigen-binding proteins (e.g., antibody or antigen-binding fragment) that bind specifically to TMPRSS2, e.g., mAb8021, mAb8028, or mAb8029, or a pharmaceutical composition thereof. The injection device may be packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antigen-binding protein, e.g., an antibody or antigen-binding fragment thereof, from a combination of the present invention, or a pharmaceutical composition thereof is an intravenous (IV) injection device. Such a device can include the antigen-binding protein or a pharmaceutical composition thereof in a cannula or trocar/needle which may be attached to a tube which may be attached to a bag or reservoir for holding fluid (e.g., saline) introduced into the body of the subject through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a subject's body. External infusion pumps are medical devices that deliver the antibody or fragment or a pharmaceutical composition thereof into a subject's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

Preparation of Human Antibodies

Methods for generating human antibodies in transgenic mice are known in the art. Any such known methods can be used in the context of the present invention to make human antibodies that specifically bind to TMPRSS2. An immunogen comprising any one of the following can be used to generate antibodies to TMPRSS2. In certain embodiments of the invention, the antibodies of the invention are obtained from mice immunized with a full length, native TMPRSS2, or with a live attenuated or inactivated virus, or with DNA encoding the protein or fragment thereof. Alternatively, the TMPRSS2 protein or a fragment thereof may be produced using standard biochemical techniques and modified and used as immunogen. In one embodiment of the invention, the immunogen is a recombinantly produced TMPRSS2 protein or fragment thereof. In certain embodiments of the invention, the immunogen may be a TMPRSS2 polypeptide vaccine. In certain embodiments, one or more booster injections may be administered. In certain embodiments, the immunogen may be a recombinant TMPRSS2 polypeptide expressed in *E. coli* or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to TMPRSS2 can be initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Anti-TMPRSS2 Antibodies Comprising Fc Variants

According to certain embodiments of the present invention, anti-TMPRSS2 antigen-binding proteins, e.g., antibodies or antigen-binding fragments, are provided comprising an Fc domain comprising one or more mutations, which, for example, enhance or diminish antibody binding to the FcRn receptor, e.g., at acidic pH as compared to neutral pH. For example, the present invention includes anti-TMPRSS2 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-TMPRSS2 antigen-binding proteins, e.g., antibodies or antigen-binding fragments, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

Anti-TMPRSS antigen-binding proteins, e.g., antibodies and antigen-binding fragments thereof, that comprise a $V_H$ and/or $V_L$ as set forth herein comprising any possible combinations of the foregoing Fc domain mutations, are contemplated within the scope of the present invention.

The present invention also includes anti-TMPRSS2 antigen-binding proteins, antibodies or antigen-binding fragments, comprising a $V_H$ set forth herein and a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., WO2014/022540).

Immunoconjugates

The invention encompasses an anti-TMPRSS2 antigen-binding proteins, e.g., antibodies or antigen-binding fragments, conjugated to another moiety, e.g., a therapeutic moiety (an "immunoconjugate"), such as a toxoid or an anti-viral drug to treat influenza virus infection. In an embodiment of the invention, an anti-TMPRSS2 antibody or fragment is conjugated to any of the further therapeutic agents set forth herein. As used herein, the term "immunoconjugate" refers to an antigen-binding protein, e.g., an antibody or antigen-binding fragment, which is chemically or biologically linked to a radioactive agent, a cytokine, an interferon, a target or reporter moiety, an enzyme, a peptide or protein or a therapeutic agent. The antigen-binding protein may be linked to the radioactive agent, cytokine, interferon, target or reporter moiety, enzyme, peptide or therapeutic agent at any location along the molecule so long as it is able to bind its target (TMPRSS2). Examples of immunoconjugates include antibody-drug conjugates and antibody-toxin fusion proteins. In one embodiment of the invention, the agent may be a second, different antibody that binds specifically to TMPRSS2. The type of therapeutic moiety that may be conjugated to the anti-TMPRSS2 antigen-binding protein (e.g., antibody or fragment) will take into account the condition to be treated and the desired therapeutic effect to be achieved. See, e.g., Arnon et al., "Monoclonal Antibodies For Immunotargeting Of Drugs In Cancer Therapy", Monoclonal Antibodies And Cancer Therapy, Reisfeld et al. (eds.), pp. 243-56 (Alan R. Liss, Inc. 1985); Hellstrom et al., "Antibodies For Drug Delivery", Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", Monoclonal Antibodies 1984: Biological And Clinical Applications, Pinchera et al. (eds.), pp. 475-506 (1985); "Analysis, Results, And Future Prospective Of The Therapeutic Use Of Radiolabeled Antibody In Cancer Therapy", Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

Multi-Specific Antibodies

The present invention includes anti-TMPRSS2 antigen-binding proteins, e.g., antibodies and antigen-binding fragments thereof, as well as methods of use thereof and methods of making such antigen-binding proteins. The term "anti-TMPRSS2" antigen-binding proteins, e.g., antibodies or antigen-binding fragments, includes multispecific (e.g., bispecific or biparatopic) molecules that include at least one first antigen-binding domain that specifically binds to TMPRSS2 (e.g., an antigen-binding domain from mAb8021, mAb8028, or mAb8029) and at least one second antigen-binding domain that binds to a different antigen or to an epitope in TMPRSS2 which is different from that of the first antigen-binding domain (e.g., influenza HA such as an antigen-binding domain from mAb8021, mAb8028, or mAb8029). In an embodiment of the invention, the first and second epitopes overlap. In another embodiment of the invention, the first and second epitopes do not overlap. For example, in an embodiment of the invention, a multispecific antibody is a bispecific IgG antibody (e.g., IgG1 or IgG4) that includes a first antigen-binding domain that binds specifically to TMPRSS2 including the heavy and light immunoglobulin chain of mAb8021, mAb8028, or mAb8029, and a second antigen-binding domain that binds specifically to influenza HA (comprising a different light and heavy immunoglobulin chain such as from mAb8021, mAb8028, or mAb8029).

mAb8021, mAb8028, and mAb8029 include multispecific molecules, e.g., antibodies or antigen-binding fragments, that include the CDR-Hs and CDR-Ls, $V_H$ and $V_L$, or HC and LC of mAb8021, mAb8028, or mAb8029, respectively (including variants thereof as set forth herein).

In an embodiment of the invention, an antigen-binding domain that binds specifically to TMPRSS, which may be included in a multispecific molecule, comprises:
(1)
(i) a heavy chain variable domain sequence that comprises CDR-H1 comprising the amino acid sequence set forth in SEQ ID NO: 4, CDR-H2 comprising the amino acid sequence set forth in SEQ ID NO: 6, and CDR-H3 comprising the amino acid sequence set forth in SEQ ID NO: 8, and
(ii) a light chain variable domain sequence that comprises CDR-L1 comprising the amino acid sequence set forth in SEQ ID NO: 12, CDR-L2 comprising the amino acid sequence set forth in SEQ ID NO: 14, and CDR-L3 comprising the amino acid sequence set forth in SEQ ID NO: 16;
or,
(2)
(i) a heavy chain variable domain sequence comprising the amino acid sequence set forth in SEQ ID NO: 2, and
(ii) a light chain variable domain sequence comprising the amino acid sequence set forth in SEQ ID NO: 10;
or,
(3)
(i) a heavy chain immunoglobulin sequence comprising the amino acid sequence set forth in SEQ ID NO: 18, and
(ii) a light chain immunoglobulin sequence comprising the amino acid sequence set forth in SEQ ID NO: 20.

In an embodiment of the invention, an antigen-binding domain that binds specifically to TMPRSS, which may be included in a multispecific molecule, comprises:
(1)
(i) a heavy chain variable domain sequence that comprises CDR-H1 comprising the amino acid sequence set forth in SEQ ID NO: 24, CDR-H2 comprising the amino acid sequence set forth in SEQ ID NO: 26, and CDR-H3 comprising the amino acid sequence set forth in SEQ ID NO: 28, and
(ii) a light chain variable domain sequence that comprises CDR-L1 comprising the amino acid sequence set forth in SEQ ID NO: 32, CDR-L2 comprising the amino acid sequence set forth in SEQ ID NO: 34, and CDR-L3 comprising the amino acid sequence set forth in SEQ ID NO: 36;
or,
(2)
(i) a heavy chain variable domain sequence comprising the amino acid sequence set forth in SEQ ID NO: 22, and
(ii) a light chain variable domain sequence comprising the amino acid sequence set forth in SEQ ID NO: 30;
or,
(3)
(i) a heavy chain immunoglobulin sequence comprising the amino acid sequence set forth in SEQ ID NO: 38, and
(ii) a light chain immunoglobulin sequence comprising the amino acid sequence set forth in SEQ ID NO: 40.

In an embodiment of the invention, an antigen-binding domain that binds specifically to TMPRSS, which may be included in a multispecific molecule, comprises:
(1)
(i) a heavy chain variable domain sequence that comprises CDR-H1 comprising the amino acid sequence set forth in SEQ ID NO: 44, CDR-H2 comprising the amino acid sequence set forth in SEQ ID NO: 46, and CDR-H3 comprising the amino acid sequence set forth in SEQ ID NO: 48, and
(ii) a light chain variable domain sequence that comprises CDR-L1 comprising the amino acid sequence set forth in SEQ ID NO: 52, CDR-L2 comprising the amino acid sequence set forth in SEQ ID NO: 54, and CDR-L3 comprising the amino acid sequence set forth in SEQ ID NO: 56;
or,
(2)
(i) a heavy chain variable domain sequence comprising the amino acid sequence set forth in SEQ ID NO: 42, and
(ii) a light chain variable domain sequence comprising the amino acid sequence set forth in SEQ ID NO: 50;
or,
(3)
(i) a heavy chain immunoglobulin sequence comprising the amino acid sequence set forth in SEQ ID NO: 58, and
(ii) a light chain immunoglobulin sequence comprising the amino acid sequence set forth in SEQ ID NO: 60.

In an embodiment of the invention, the multispecific antibody or fragment includes more than two different binding specificities (e.g., a trispecific molecule), for example, one or more additional antigen-binding domains which are the same or different from the first and/or second antigen-binding domain.

In an embodiment of the invention, a multispecific molecule comprises, in addition to an antigen-binding site that bind specifically to TMPRSS2, an antigen-binding site that binds specifically to a coronavirus spike protein taken from an antibody selected from the group consisting of: H4sH15188P; H1H15188P; H1H15211P; H1H15177P; H4sH15211P; H1H15260P2; H1H15259P2; H1H15203P; H4sH15260P2; H4sH15231P2; H1H15237P2; H1H15208P; H1H15228P2; H1H15233P2; H1H15264P2; H1H15231P2; H1H15253P2; H1H15215P; and H1H15249P2, as set forth in International patent application publication no. WO/2015/179535.

In an embodiment of the invention, a multispecific molecule comprises, in addition to an antigen-binding site that bind specifically to TMPRSS2, an antigen-binding site that binds specifically to influenza HA taken from an antibody selected from the group consisting of:

H1H14611N2; H1H14612N2; H1H11723P; H1H11729P; H1H11820N; H1H11829N; H1H11829N2; H2aM11829N; H2M11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; and H1H18335B; as set forth in International patent application publication no. WO2016/100807 (e.g., the CDR-Hs, $V_H$ or heavy chain thereof; and the CDR-Ls, $V_L$ or light chain thereof).

In an embodiment of the invention, a multispecific molecule comprises, in addition to an antigen-binding site that binds specifically to TMPRSS2, an antigen-binding site that binds specifically to influenza Group II HA protein, e.g., which comprises $V_H$ and $V_L$ of H1H14611N2; or a heavy chain immunoglobulin comprising CDR-H1, CDR-H2 and CDR-H3 of H1H14611N2 and a light chain immunoglobulin comprising CDR-L1, CDR-L2 and CDR-L3 of H1H14611N2.

In an embodiment of the invention, a multispecific molecule comprises, in addition to an antigen-binding site that bind specifically to TMPRSS2, an antigen-binding site that binds specifically to influenza Group II HA protein, e.g., which comprises $V_H$ and $V_L$ of H1H14612N2; or a heavy chain immunoglobulin comprising CDR-H1, CDR-H2 and CDR-H3 of H1H14612N2 and a light chain immunoglobulin comprising CDR-L1, CDR-L2 and CDR-L3 of H1H14612N2.

In an embodiment of the invention, a multispecific molecule comprises, in addition to an antigen-binding site that bind specifically to TMPRSS2, an antigen-binding site that binds specifically to influenza Group I HA protein, e.g., which comprises $V_H$ and $V_L$ of H1H11729P; or a heavy chain immunoglobulin comprising CDR-H1, CDR-H2 and CDR-H3 of H1H11729P and a light chain immunoglobulin comprising CDR-L1, CDR-L2 and CDR-L3 of H1H11729P.

In one embodiment of the invention, a bispecific antigen-binding fragment comprises a first scFv (e.g., comprising $V_H$ and $V_L$ of mAb8021, mAb8028, or mAb8029) having binding specificity for a first epitope (e.g., TMPRSS2) and a second scFv (e.g., comprising $V_H$ and $V_L$ of an anti-influenza HA antibody) having binding specificity for a second, different epitope. For example, in an embodiment of the invention, the first and second scFv are tethered with a linker, e.g., a peptide linker (e.g., a GS linker such as (GGGGS)$_n$ (SEQ ID NO: 62) wherein n is, for example, 1, 2, 3, 4, 5, 6, 7, 8, 9 or 10). Other bispecific antigen-binding fragments include an F(ab)$_2$ of a bispecific IgG antibody which comprises the heavy and light chain CDRs of mAb8021 or mAb8028 or mAb8029 and of another antibody that binds to a different epitope.

Therapeutic Methods

The present invention provides methods for treating or preventing viral infection or cancer (e.g., prostate cancer) by administering a therapeutically effective amount of anti-TMPRSS2 antigen-binding protein, e.g., antibody or antigen-binding fragment, (e.g., mAb8021, mAb8028, or mAb8029) to a subject (e.g., a human) in need of such treatment or prevention.

Coronavirus or influenza virus infection may be treated or prevented, in a subject, by administering an anti-TMPRSS2 antigen-binding protein of the present invention to a subject. Influenza viruses are classified into types A, B and C on the basis of their core proteins. The subtypes of influenza A viruses are determined by envelope glycoproteins possessing either hemagglutinin (HA) or neuraminidase (NA) activity. There are several HA subtypes (e.g., HA1, HA2, HA3, HA4, HA5, HA6, HA7, HA8, HA9, HA10, HA11, HA12, HA13, HA14, HA15, HA16, HA17 or HA18—these subtypes may be designated as H1, H2, H3, etc.) and NA subtypes (e.g., NA1, NA2, NA3, NA4, NA5, NA6, NA7, NA8, NA9, NA10 or NA11—these subtypes may be designated as N1, N2, N3, etc.) of influenza A viruses which are used to designate influenza A subtype. For example, Influenza A virus H1N1 and H3N2 are commonly known human pathogens. Humans are commonly infected by viruses of the subtypes H1, H2 or H3, and N1 or N2. The present invention includes methods for treating or preventing infection with an influenza virus subtype discussed herein. Multispecific antibodies and antigen-binding fragments thereof that bind to TMPRSS2, in an embodiment of the invention, also bind to spike protein of a coronavirus (e.g., SARS-CoV-2, MERS-CoV, or SARS-CoV) or to HA and/or to NA of an influenza virus (e.g., an influenza virus of a subtype set forth herein).

An effective or therapeutically effective dose of anti-TMPRSS2 antigen-binding protein, e.g., antibody or antigen-binding fragment (e.g., mAb8021 or mAb8028 or mAb8029), for treating or preventing a viral infection refers to the amount of the antibody or fragment sufficient to alleviate one or more signs and/or symptoms of the infection in the treated subject, whether by inducing the regression or elimination of such signs and/or symptoms or by inhibiting the progression of such signs and/or symptoms. The dose amount may vary depending upon the age and the size of a subject to be administered, target disease, conditions, route of administration, and the like. In an embodiment of the invention, an effective or therapeutically effective dose of antibody or antigen-binding fragment thereof of the present invention, for treating or preventing viral infection, e.g., in an adult human subject, is about 0.01 to about 200 mg/kg, e.g., up to about 150 mg/kg. In an embodiment of the invention, the dosage is up to about 10.8 or 11 grams (e.g., about 1, 2, 3, 4, 5, 6, 7, 8, 9, 10 or 11 grams). Depending on the severity of the infection, the frequency and the duration of the treatment can be adjusted. In certain embodiments, the antigen-binding protein of the present invention can be administered at an initial dose, followed by one or more secondary doses. In certain embodiments, the initial dose may be followed by administration of a second or a plurality of subsequent doses of antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of a disease or disorder such as viral infection or cancer. The subject may have a viral infection, e.g., an influenza infection, or be predisposed to developing an infection. Subjects predisposed to developing an infection, or subjects who may be at elevated risk for contracting an infection (e.g., of coronavirus or influenza virus), include subjects with compromised immune systems because of autoimmune disease, subjects receiving immunosuppressive therapy (for example, following organ transplant), subjects afflicted with human immunodeficiency syndrome (HIV) or acquired immune deficiency syndrome (AIDS), subjects with forms of anemia that deplete or destroy white blood cells, subjects receiving radiation or chemotherapy, or subjects afflicted with an inflammatory disorder. Additionally, subjects of very young (e.g., 5 years of age or younger) or old age (e.g., 65 years of age or older) are at increased risk. Moreover, a subject may be at risk of contracting a viral infection due to proximity to an outbreak of the disease, e.g. subject resides in a densely-populated city or in close proximity to subjects having confirmed or suspected infections of a virus, or choice of employment, e.g. hospital worker, pharmaceutical researcher, traveler to infected area, or frequent flier.

"Treat" or "treating" means to administer an anti-TMPRSS2 antigen-binding protein, e.g., antibody or antigen-binding fragment of the present invention (e.g., mAb8021 or mAb8028 or mAb8029), to a subject having one or more signs or symptoms of a disease or infection, e.g., viral infection, for which the antigen-binding protein is effective when administered to the subject at an effective or therapeutically effective amount or dose (as discussed herein).

The present invention also encompasses prophylactically administering an anti-TMPRSS2 antigen-binding protein, e.g., antibody or antigen-binding fragment thereof of the present invention (e.g., mAb8021 or mAb8028 or mAb8029), to a subject who is at risk of viral infection so as to prevent such infection. Passive antibody-based immunoprophylaxis has proven an effective strategy for preventing subject from viral infection. See e.g., Berry et al., Passive broad-spectrum influenza immunoprophylaxis. Influenza Res Treat. 2014; 2014:267594. Epub 2014 Sep. 22; and Jianqiang et al., Passive immune neutralization strategies for prevention and control of influenza A infections, Immunotherapy. 2012 February; 4(2): 175-186; Prabhu et al., Antivir Ther. 2009; 14(7):911-21, Prophylactic and therapeutic efficacy of a chimeric monoclonal antibody specific for H5 hemagglutinin against lethal H5N1 influenza. "Prevent" or "preventing" means to administer an anti-TMPRSS2 antigen-binding protein, e.g., antibody or antigen-binding fragment of the present invention (e.g., mAb8021 or mAb8028 or mAb8029), to a subject to inhibit the manifestation of a disease or infection (e.g., viral infection) in the body of a subject, for which the antigen-binding protein is effective when administered to the subject at an effective or therapeutically effective amount or dose (as discussed herein).

In an embodiment of the invention, a sign or symptom of a viral infection in a subject is survival or proliferation of virus in the body of the subject, e.g., as determined by viral titer assay (e.g., coronavirus or influenza virus propagation in embryonated chicken eggs, coronavirus spike protein assay, or influenza virus hemagglutination assay). Other signs and symptoms of viral infection are discussed herein.

The present invention provides a method for treating or preventing viral infection (e.g., influenza virus or coronavirus infection) or for inducing the regression or elimination or inhibiting the progression of at least one sign or symptom of viral infection such as:

fever or feeling feverish/chills;
cough;
sore throat;
runny or stuffy nose;
sneezing;
muscle or body aches;
headaches;
fatigue (tiredness);
vomiting;
diarrhea;
respiratory tract infection;
chest discomfort;
shortness of breath;
bronchitis; and/or
pneumonia, which sign or symptom is secondary to viral infection, in a subject in need thereof (e.g., a human), by administering a therapeutically effective amount of anti-TMPRSS2 antigen-binding protein (e.g., mAb8021 or mAb8028 or mAb8029) to the subject, for example, by injection of the protein into the body of the subject.

The present invention also includes methods for treating or preventing cancer, e.g., metastatic cancer, e.g., prostate cancer (e.g., which is characterized by expression of a TMPRSS2:ERG fusion), colon cancer, lung cancer, pancreas cancer, urinary tract cancer, breast cancer, ovarian cancer, prostate adenocarcinoma, renal cell carcinoma, colorectal adenocarcinoma, lung adenocarcinoma, lung squamous cell carcinoma and/or pleural mesothelioma, in a subject, by administering a therapeutically effective amount of TMPRSS2 antigen-binding protein (e.g., mAb8021 or mAb8028 or mAb8029) to the subject, for example, by injection of the protein into the body of the subject. In an embodiment of the invention, the subject is also administered the TMPRSS2 antigen-binding protein in association with a further therapeutic agent, for example, an anti-cancer therapeutic agent. In an embodiment of the invention, the cancer is a tumor whose cells express TMPRSS2 or a variant thereof.

Combinations and Pharmaceutical Compositions

To prepare pharmaceutical compositions of the anti-TMPRSS2 antigen-binding proteins, e.g., antibodies and antigen-binding fragments thereof (e.g., mAb8021 or mAb8028 or mAb8029), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical composition is sterile. Such compositions are part of the present invention.

The scope of the present invention includes desiccated, e.g., freeze-dried, compositions comprising an anti-TMPRSS2 antigen-binding proteins, e.g., antibody or antigen-binding fragment thereof (e.g., mAb8021 or mAb8028 or mAb8029), or a pharmaceutical composition thereof that includes a pharmaceutically acceptable carrier but substantially lacks water.

In a further embodiment of the invention, a further therapeutic agent that is administered to a subject in association with an anti-TMPRSS2 antigen-binding protein, e.g., antibody or antigen-binding fragment thereof (e.g., mAb8021 or mAb8028 or mAb8029), disclosed herein is administered to the subject in accordance with the Physicians' Desk Reference 2003 (Thomson Healthcare; 57$^{th}$ edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial.

The present invention provides methods for administering an anti-TMPRSS2 antigen-binding protein, e.g., antibody or antigen-binding fragment thereof (e.g., mAb8021 or mAb8028 or mAb8029), comprising introducing the protein into the body of a subject. For example, the method comprises piercing the body of the subject with a needle of a syringe and injecting the antigen-binding protein into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-TMPRSS2 antigen-binding proteins, e.g., antibodies or antigen-binding fragments thereof (e.g., mAb8021, mAb8028 or mAb8029), polypeptides (e.g., an HC, LC, $V_H$ or $V_L$ of mAb8021, mAb8028, or mAb8029) or polynucleotides or vectors set forth herein or a pharmaceutical composition thereof comprising a pharmaceutically acceptable carrier.

In an embodiment of the invention, an anti-TMPRSS2 antigen-binding protein, e.g., antibody or antigen-binding fragment thereof of the present invention (e.g., mAb8021, mAb8028, or mAb8029), is in association with one or more further therapeutic agents. For example, in an embodiment of the invention, the further therapeutic agent is an anti-viral drug and/or a vaccine. As used herein, the term "anti-viral drug" refers to any anti-infective drug or therapy used to treat, prevent, or ameliorate a viral infection in a subject. The term "anti-viral drug" includes, but is not limited to a cationic steroid antimicrobial, leupeptin, aprotinin, amantadine, rimantadine, oseltamivir, zanamivir, ribavirin, or interferon-alpha2b. Methods for treating or preventing virus (e.g., coronavirus or influenza virus) infection in a subject in need of said treatment or prevention by administering mAb8021, mAb8028, or mAb8029 in association with a further therapeutic agent are part of the present invention.

For example, in an embodiment of the invention, the further therapeutic agent is a vaccine, e.g., a coronavirus vaccine or an influenza vaccine. In an embodiment of the invention, a vaccine is an inactivated/killed virus vaccine, a live attenuated virus vaccine or a virus subunit vaccine.

For example, in an embodiment of the invention, the further therapeutic agent is:

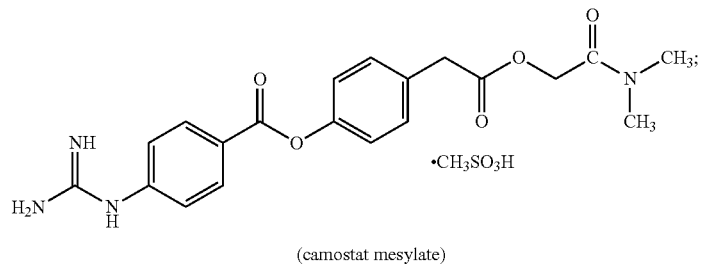

(camostat mesylate)

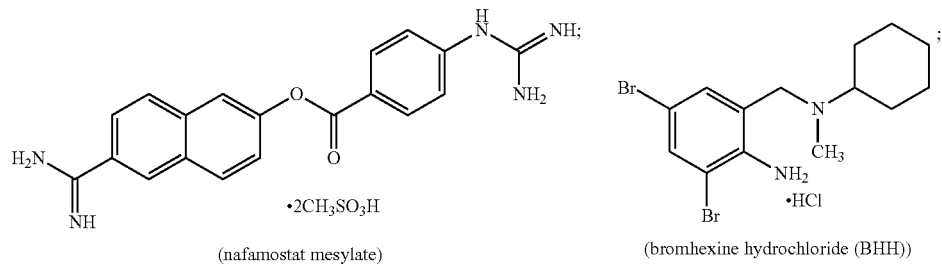

(nafamostat mesylate)

(bromhexine hydrochloride (BHH))

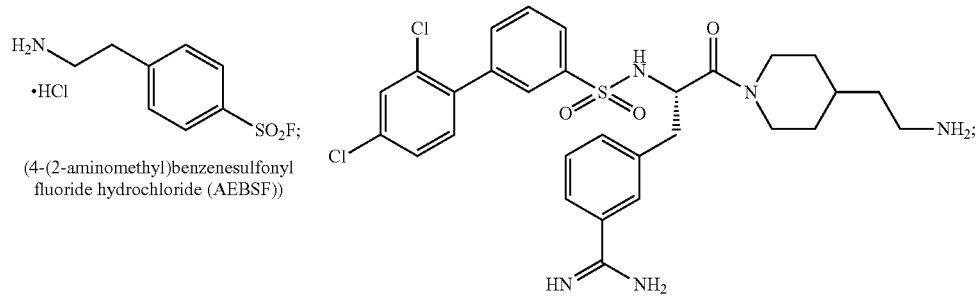

(4-(2-aminomethyl)benzenesulfonyl fluoride hydrochloride (AEBSF))

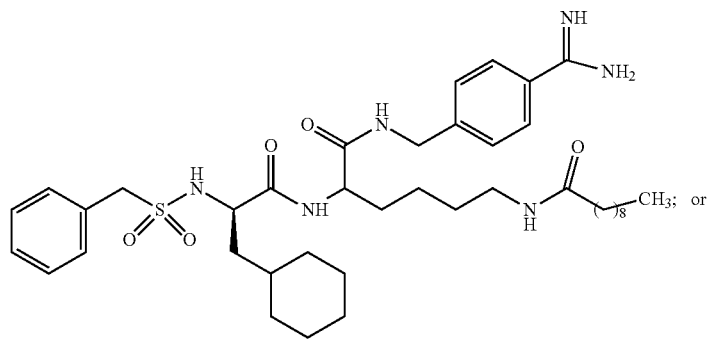

or

-continued

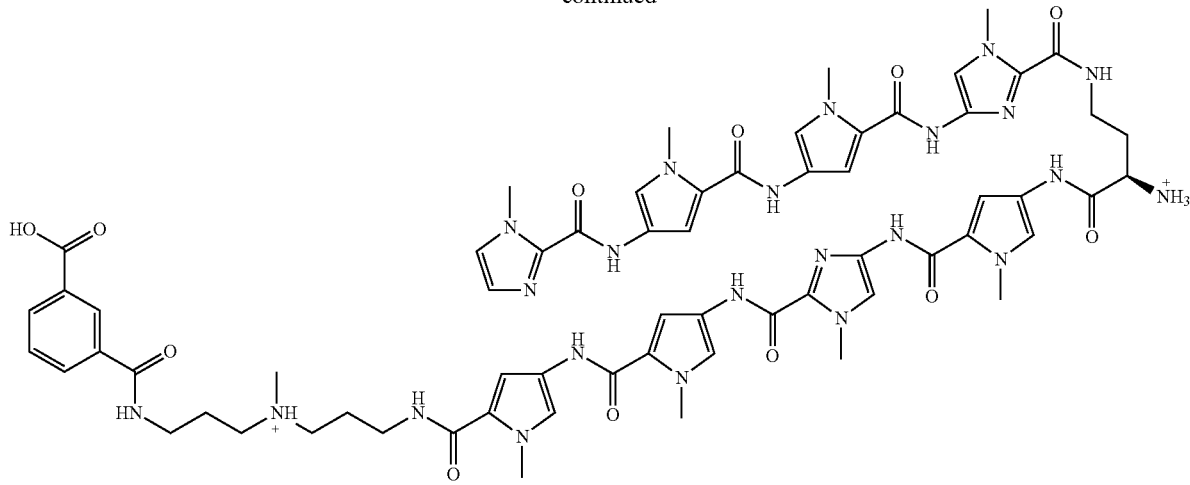

In an embodiment of the invention, the anti-viral drug is an antibody or antigen-binding fragment that binds specifically to coronavirus, e.g., CoV-S. For example, in an embodiment of the invention, the anti-CoV-S antibody is any one of: H4sH15188P; H1H15188P; H1H15211P; H1H15177P; H4sH15211P; H1H15260P2; H1H15259P2; H1H15203P; H4sH15260P2; H4sH15231P2; H1H15237P2; H1H15208P; H1H15228P2; H1H15233P2; H1H15264P2; H1H15231P2; H1H15253P2; H1H15215P; and H1H15249P2, as set forth in International patent application publication no. WO/2015/179535, or an antigen-binding fragment thereof, e.g., wherein the antibody or fragment comprises a light chain immunoglobulin that includes CDR-L1, CDR-L2 and CDR-L3 (e.g., the $V_L$ or light chain thereof); and a heavy chain that includes CDR-H1, CDR-H2 and CDR-H3 (e.g., the $V_H$ or heavy chain thereof) of any of the foregoing anti-CoV-S antibodies.

In an embodiment of the invention, the anti-viral drug is an antibody or antigen-binding fragment that binds specifically to influenza virus, e.g., influenza HA. For example, in an embodiment of the invention, the anti-HA antibody is any one of H1H14611N2; H1H14612N2; H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B;

H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; or H1H18335B; as set forth in International patent application publication no. WO2016/100807; or an antigen-binding fragment thereof, e.g., wherein the antibody or fragment comprises a light chain immunoglobulin that includes CDR-L1, CDR-L2 and CDR-L3 (e.g., the $V_L$ or light chain thereof); and a heavy chain that includes CDR-H1, CDR-H2 and CDR-H3 (e.g., the $V_H$ or heavy chain thereof) of any of the foregoing anti-influenza HA antibodies.

In an embodiment of the invention, a further therapeutic agent is an antibody or antigen-binding fragment that binds to influenza Group II HA protein such as H1H14611N2; or an antibody or fragment that comprises $V_H$ and $V_L$ of H1H14611N2; or a heavy chain immunoglobulin comprising CDR-H1, CDR-H2 and CDR-H3 of H1H14611N2 and a light chain immunoglobulin comprising CDR-L1, CDR-L2 and CDR-L3 of H1H14611N2. "H1H14611N2" refers to any anti-group II HA antibody comprising such sequences.

In an embodiment of the invention, a further therapeutic agent is an antibody or antigen-binding fragment that binds to influenza Group II HA protein such as H1H14612N2; or an antibody or fragment that comprises $V_H$ and $V_L$ of H1H14612N2; or a heavy chain immunoglobulin comprising CDR-H1, CDR-H2 and CDR-H3 of H1H14612N2 and a light chain immunoglobulin comprising CDR-L1, CDR-L2 and CDR-L3 of H1H14612N2. "H1H14612N2" refers to any anti-group II HA antibody comprising such sequences.

In an embodiment of the invention, a further therapeutic agent is an antibody or antigen-binding fragment that binds to influenza Group I HA protein such as H1H11729P; or an antibody or fragment that comprises $V_H$ and $V_L$ of H1H11729P; or a heavy chain immunoglobulin comprising CDR-H1, CDR-H2 and CDR-H3 of H1H11729P and a light chain immunoglobulin comprising CDR-L1, CDR-L2 and CDR-L3 of H1H11729P. "H1H11729P" refers to any anti-group I HA antibody comprising such sequences.

In a certain embodiment of the invention, the further therapeutic agent is not amantadine, rimantadine, oseltamivir, zanamivir, aprotinin, leupeptin, a cationic steroid antimicrobial, an influenza vaccine (e.g., killed, live, attenuated whole virus or subunit vaccine), or an antibody against influenza virus (e.g., an anti-hemagglutinin antibody).

The term "in association with" indicates that the components, an anti-TMPRSS2 antigen-binding protein, e.g., antibody or antigen-binding fragment thereof of the present invention, along with another agent such as oseltamivir, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein an anti-TMPRSS2 antibody or antigen-binding fragment thereof.

Kits

Further provided are kits comprising one or more components that include, but are not limited to, an anti-TMPRSS2 antigen-binding protein, e.g., an antibody or antigen-binding fragment as discussed herein (e.g., mAb8021, mAb8028, or mAb8029), in association with one or more additional components including, but not limited to, a further therapeutic agent, as discussed herein. The antigen-binding protein and/or the further therapeutic agent can be formulated as a single composition or separately in two or more compositions, e.g., with a pharmaceutically acceptable carrier, in a pharmaceutical composition.

In one embodiment of the invention, the kit includes an anti-TMPRSS2 antigen-binding protein, e.g., an antibody or antigen-binding fragment thereof of the invention (e.g., mAb8021, mAb8028, or mAb8029), or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an anti-TMPRSS2 antigen-binding protein, e.g., antibody or antigen-binding fragment thereof of the invention (e.g., mAb8021, mAb8028, or mAb8029), or pharmaceutical composition thereof in combination with one or more further therapeutic agents formulated together, optionally, in a pharmaceutical composition, in a single, common container.

If the kit includes a pharmaceutical composition for parenteral administration to a subject, the kit can include a device (e.g., an injection device) for performing such administration. For example, the kit can include one or more hypodermic needles or other injection devices as discussed above containing the anti-TMPRSS2 antigen-binding protein, e.g., antibody or antigen-binding fragment thereof of the present invention (e.g., mAb8021, mAb8028, or mAb8029).

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Diagnostic Uses of the Antibodies

The anti-TMPRSS2 antigen-binding proteins, e.g., antibodies or antigen-binding fragments thereof of the present invention (e.g., mAb8021, mAb8028, or mAb8029), may be used to detect and/or measure TMPRSS2 in a sample. Exemplary assays for TMPRSS2 may include, e.g., contacting a sample with an anti-TMPRSS2 antigen-binding protein of the invention, wherein the anti-TMPRSS2 antigen-binding protein is labeled with a detectable label or reporter molecule or used as a capture ligand to selectively isolate TMPRSS2 from samples. The presence of an anti-TMPRSS2 antigen-binding protein complexed with TMPRSS2 indicates the presence of TMRPSS2 in the sample. Alternatively, an unlabeled anti-TMPRSS2 antibody can be used in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure TMPRSS2 in a sample include enzyme-linked immunosorbent assay (ELISA), radioimmunoassay (RIA), and fluorescence-activated cell sorting (FACS). Thus, the present invention includes a method for detecting the presence of TMPRSS2 polypeptide in a sample comprising contacting the sample with an anti-TMPRSS2 antigen-binding protein and detecting the presence of a TMPRSS/anti-TMPRSS2 antigen-binding protein wherein the presence of the complex indicates the presence of TMPRSS2.

The present invention includes cell-based ELISA methods using the anti-TMPRSS2 antigen-binding proteins, e.g., antibodies and antigen-binding fragments thereof of the present invention (e.g., mAb8021, mAb8028, or mAb8029), to detect the presence of TMPRSS2 on a cell. In an embodiment of the invention, the method includes the steps:

(i) contacting cells immobilized to a solid surface (e.g., a microplate) to be tested for the presence of TMPRSS2 with an anti-TMPRSS2 antigen-binding protein of the present invention;
(ii) optionally washing the mixture to remove unbound anti-TMPRSS2 antigen-binding protein;
(iii) contacting the anti-TMPRSS2 antigen-binding protein with a labeled secondary antibody or antigen-binding fragment thereof that binds to the anti-TMPRSS2 antigen-binding protein;
(iv) optionally washing the complex to remove unbound antigen-binding protein; and
(v) detecting the presence of the label on the secondary antibody or fragment, wherein detection of the label indicates that the cells contain TMPRSS2. For example, the present invention includes such cell-based ELISA methods for identifying TMPRSS2$^+$ cells in a sample.

An anti-TMPRSS2 antigen-binding protein of the invention (e.g., mAb8021, mAb8028, or mAb8029) may be used in a Western blot or immune-protein blot procedure for detecting the presence of TMPRSS2 or a fragment thereof in a sample. Such a procedure forms part of the present invention and includes the steps of e.g.:

(1) providing a membrane or other solid substrate comprising a sample to be tested for the presence of TMPRSS2, e.g., optionally including the step of transferring proteins from a sample to be tested for the presence of TMPRSS2 (e.g., from a PAGE or SDS-PAGE electrophoretic separation of the proteins in the sample) onto a membrane or other solid substrate using a method known in the art (e.g., semi-dry blotting or tank blotting); and contacting the membrane or other solid substrate to be tested for the presence of TMPRSS2 or a fragment thereof with an anti-TMPRSS2 antigen-binding protein of the invention.

Such a membrane may take the form, for example, of a nitrocellulose or vinyl-based (e.g., polyvinylidene fluoride (PVDF)) membrane to which the proteins to be tested for the presence of TMPRSS2 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-TMPRSS2 antigen-binding protein, the membrane is optionally blocked, e.g., with non-fat dry milk or the like so as to bind non-specific protein binding sites on the membrane.

(2) washing the membrane one or more times to remove unbound anti-TMPRSS2 antigen-binding protein and other unbound substances; and
(3) detecting the bound anti-TMPRSS2 antigen-binding protein.

Detection of the bound antigen-binding protein indicates that the TMPRSS2 protein is present on the membrane or substrate and in the sample. Detection of the bound antigen-binding protein may be by binding the antigen-binding protein with a secondary antibody (an anti-immunoglobulin antibody) which is detectably labeled and, then, detecting the presence of the secondary antibody label.

The anti-TMPRSS2 antigen-binding proteins (e.g., antibodies and antigen-binding fragments (e.g., mAb8021, mAb8028, or mAb8029)) disclosed herein may also be used for immunohistochemistry. Such a method forms part of the present invention and comprises, e.g., (1) contacting tissue to be tested for the presence of TMPRSS2 protein with an anti-TMPRSS2 antigen-binding protein of the invention; and
(2) detecting the antigen-binding protein on or in the tissue.

If the antigen-binding protein itself is detectably labeled, it can be detected directly. Alternatively, the antigen-binding protein may be bound by a detectably labeled secondary antibody wherein the label is then detected.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to TMPRSS2

Human antibodies to TMPRSS2 were generated in a VELOCIMMUNE® mouse comprising DNA encoding human immunoglobulin heavy and kappa light chain variable regions. The mice were immunized with vectors expressing TMPRSS2, followed by a booster dose of TMPRSS2. The antibody immune response was monitored by a TMPRSS2-specific immunoassay. Anti-TMPRSS2 antibodies were isolated directly from antigen-positive mouse B cells without fusion to myeloma cells, as described in U.S. Pat. No. 7,582,298, herein specifically incorporated by reference in its entirety. Using this method, fully human anti-TMPRSS2 antibodies (i.e., antibodies possessing human variable domains and human constant domains) were obtained.

Exemplary antibodies described herein are designated mAb8028, mAb8021, and mAb8029. The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions (HCVR and LCVR, respectively) and CDRs (HCDR-1, HCDR-2, HCDR-3, LCDR-1, LCDR-2, and LCDR-3), as well as the heavy chain (HC) and light chain (LC) sequences, of the exemplary anti-TMPRSS2 antibodies. The corresponding nucleic acid sequence identifiers are set forth in Table 2.

Antibodies disclosed herein have fully human variable regions but can have mouse constant regions (e.g., a mouse IgG1 Fc or a mouse IgG2 Fc (a or b isotype)) or human constant regions (e.g., a human IgG1 Fc or a human IgG4 Fc). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2 will remain the same, and the binding properties to antigen are expected to be identical or substantially similar regardless of the nature of the Fc domain.

Example 3: In Vitro Multicycle Replication

The ability of the influenza virus, Influenza A A/Puerto Rico/08/1934 (H1_PR34), to replicate in Calu3 cells after treatment with mAb8021, mAb8028, or mAb8029 was assessed.

TABLE 3

| Reagents used | |
|---|---|
| Description | Vendor |
| Calu-3 cells | ATCC |
| EMEM | Gibco |
| Non-essential amino acids | Invitrogen |
| F12 | Gibco |
| 3.5 mL 30% low IgG BSA | Sigma |
| Pen/Strep | Gibco |
| Low IgG BSA | Sigma |
| PBS | Life Technologies |
| Fetal Bovine Serum | Life Technologies |
| Influenza A A/Puerto Rico/08/1934 (H1_PR34) | ATCC |
| Anti-influenza NP (mouse) | Millipore |

Calu-3 cells were seeded at 40,000 cells/well in a 96-well plate in DMEM:F12 medium with 5% FBS. The next day, influenza virus was diluted to a MOI of 0.01 and antibodies were diluted to 25 μg/mL. The HA antibody was pre-incubated with an influenza virus for one hour at 37° C. in a separate plate. After the pre-incubation period, uninfected Calu-3 cells were treated with either the anti-HA antibody/virus mixture, or with one of the anti-TMPRSS2 antibodies mAb8021, mAb8028, or mAb8029 in combination with the influenza virus. The treated Calu-3 cells were then incubated for one hour. After the hour-long infection, the cells were washed three times with PBS and fresh antibody (anti-HA or anti-TMPRSS2, consistent with the previous antibody) was added along with new medium to each well. Additional

TABLE 1

Amino acid sequence identifiers

| | SEQUENCE IDENTIFIER HCVR | CDR-H1 | CDR-H2 | CDR-H3 | LCVR | CDR-L1 | CDR-L2 | CDR-L3 | HC | LC |
|---|---|---|---|---|---|---|---|---|---|---|
| mAb8028 | 2 | 4 | 6 | 8 | 10 | 12 | 14 | 16 | 18 | 20 |
| mAb8021 | 22 | 24 | 26 | 28 | 30 | 32 | 34 | 36 | 38 | 40 |
| mAb8029 | 42 | 44 | 46 | 48 | 50 | 52 | 54 | 56 | 58 | 60 |

TABLE 2

Nucleic acid sequence identifiers

| | SEQUENCE IDENTIFIER | | | | | | | | | |
|---|---|---|---|---|---|---|---|---|---|---|
| | HCVR | CDR-H1 | CDR-H2 | CDR-H3 | LCVR | CDR-L1 | CDR-L2 | CDR-L3 | HC | LC |
| mAb8028 | 1 | 3 | 5 | 7 | 9 | 11 | 13 | 15 | 17 | 19 |
| mAb8021 | 21 | 23 | 25 | 27 | 29 | 31 | 33 | 35 | 37 | 39 |
| mAb8029 | 41 | 43 | 45 | 47 | 49 | 51 | 53 | 55 | 57 | 59 | antibody was added at 24 and 48 hours post-infection. At 72 hours post-infection, the cells were stained with an anti-NP and imaged on a CTL-ImmunoSpot® S6 Universal Analyzer (Cellular Technology Limited, Cleveland, Ohio).

Calu-3 is an immortalized human airway epithelial cell line which has been shown to allow multicycle replication of human influenza viruses in the absence of exogenous trypsin (Zeng et al., Highly pathogenic avian influenza H5N1 viruses elicit an attenuated type I interferon response in polarized human bronchial epithelial cells. J Virol. 81:12439-12449 (2007)). In addition, Calu-3 cells have been shown to express TMPRSS2, which is important for testing anti-TMPRSS2 antibodies. Although these antibodies were assayed for their ability to prevent the multicycle replication of influenza PR8 virus, the skilled worker will appreciate that TMPRSS2 is also involved in coronavirus infection and, therefore, that blocking TMPRSS2 would have a similar effect on coronavirus infection. Moreover, blocking TMPRSS2 may be beneficial because it has the potential to inhibit broader viral infectivity than blocking a specific viral protein. As a positive control, an anti-HA neutralizing antibody was used for inhibition of infectivity. As a negative control, an isotype control antibody was used. Imaging of the infected cells was performed on a CTL-ImmunoSpot® S6 Universal Analyzer (Cellular Technology Limited, Cleveland, Ohio). TMPRSS2 mAbs demonstrated inhibition of influenza infection, as observed by examining the differences in the number of infected cells between the anti-TMPRSS2 mAb-treated cells and isotype control-treated cells. The relative degree of mAb-mediated inhibition of virus replication is reported in Table 4, below.

TABLE 4

Viral inhibition by mAb8021, mAb8028, and mAb8029

| mAb | mAb target | Level of virus inhibition |
| --- | --- | --- |
| mAb8021 | TMPRSS2 | +++ |
| mAb8028 | TMPRSS2 | +++ |
| mAb8029 | TMPRSS2 | +++ |
| Positive Control | Influenza HA | ++++ |
| Negative Control | Isotype control | − |

Level of virus inhibition relative to infected, untreated control.
No inhibition (−), no virus positive cells (++++), few virus positive cells (+++).

Example 3: Binding Kinetics of Anti-TMPRSS2 Antibodies

The equilibrium dissociation constant ($K_D$) for TMPRSS2 binding to different TMPRSS2 monoclonal antibodies (mAbs) was determined with a real-time surface plasmon resonance biosensor using a Biacore T200 instrument. All binding studies were performed in 10 mM HEPES, 150 mM NaCl, and 0.05% v/v Surfactant Tween-20, pH 7.4 (HBS-P) running buffer at 25° C. and 37° C. The Biacore CM5 sensor chip surface was first derivatized by amine coupling with anti-human Fc mAb (REGN2567) to capture different TMPRSS2 mAbs expressed with a C-terminal myc-myc-hexahistidine (MMH) tag. Different concentrations (100-3.7 nM, 3-fold serial dilution) of the ectodomain of human TMPRSS2-myc-myc-His (hTMPRSS2-MMH), *Macaca fascicularis* TMPRSS2-MMH (mfTMPRSS2-MMH), rat TMPRSS2-MMH (rTMPRSS2-MMH), or mouse TMPRSS2-MMH (mTMPRSS2-MMH), prepared in HBS-P running buffer were injected over the TMPRSS2 mAb captured surface for 150 sec at a flow rate of 30 μL/min and their dissociation in HBS-P running buffer was monitored for 10 minutes. At the end of each cycle, the TMPRSS2 mAb captured surface was regenerated using a 12 sec injection of 20 mM phosphoric acid.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life ($t\frac{1}{2}$) were calculated from the kinetic rates as:

$$K_D(M) = \frac{kd}{ka}, \text{ and } t^{\frac{1}{2}}(\min) = \frac{\ln(2)}{60 * kd}$$

Binding kinetics parameters for TMPRSS2 binding to different TMPRSS2 mAbs of the invention at 25° C. and 37° C. are shown in Tables 5 through 12. Both mAb8021 and mAb8029 exhibited strong binding to TMPRSS2, and mAb8021 in particular exhibited preferential binding to hTMPRSS2 and mfTMPRSS2 over rTMPRSS2 and mTMPRSS2.

TABLE 5

Binding kinetics of anti-TMPRSS2 mAbs binding to hTMPRSS2-MMH at 25° C.

| mAb Captured | mAb Capture Level (RU) | 100 nM hTMPRSS2-MMH Bound (RU) | $k_\alpha$ (1/Ms) | $k_d$ (1/s) | $K_D$ (M) | $t\frac{1}{2}$ (min) |
| --- | --- | --- | --- | --- | --- | --- |
| Positive control* | 226.2 ± 1.9 | 58.4 | 6.02E ± 06 | 4.09E−04 | 6.80E−11 | 28.2 |
| mAb8021 | 199.4 ± 1.5 | 62.6 | 3.08E ± 06 | 9.19E−05 | 2.99E−11 | 125.7 |
| mAb8029 | 234.6 ± 2 | 64.5 | 2.18E ± 06 | 1.29E−04 | 5.92E−11 | 89.5 |

*Positive control antibody H4H7017N, as described in International Patent Pub. No. WO/2019/147831

TABLE 6

Binding kinetics of anti-TMPRSS2 mAbs binding to hTMPRSS2-MMH at 37° C.

| mAb Captured | mAb Capture Level (RU) | 100 nM hTMPRSS2-MMH Bound (RU) | $k_a$ (1/Ms) | $k_d$ (1/s) | $K_D$ (M) | $t^{1/2}$ (min) |
|---|---|---|---|---|---|---|
| Positive control* | 144.9 ± 1.3 | 28.5 | 9.93E + 06 | 2.21E−03 | 2.22E−10 | 5.2 |
| mAb8021 | 134.9 ± 1.1 | 40.1 | 4.17E + 06 | 2.61E−04 | 6.27E−11 | 44.2 |
| mAb8029 | 147.8 ± 0.5 | 35.9 | 3.12E + 06 | 6.73E−04 | 2.16E−10 | 17.2 |

*Positive control antibody H4H7017N, as described in International Patent Pub. No. WO/2019/147831

TABLE 7

Binding kinetics of anti-TMPRSS2 mAbs binding to mfTMPRSS2-MMH at 25° C.

| mAb Captured | mAb Capture Level (RU) | 100 nM mfTMPRSS2-MMH Bound (RU) | $k_a$ (1/Ms) | $k_d$ (1/s) | $K_D$ (M) | $t^{1/2}$ (min) |
|---|---|---|---|---|---|---|
| Positive control* | 231.4 ± 4.4 | 47.2 | 6.60E ± 06 | 8.78E−03 | 1.33E−09 | 1.3 |
| mAb8021 | 201.5 ± 1.9 | 63.4 | 4.48E ± 06 | 1.13E−04 | 2.52E−11 | 102.2 |
| mAb8029 | 233.5 ± 2.2 | 66.7 | 3.20E ± 06 | 1.96E−04 | 6.09E−11 | 59.1 |

*Positive control antibody H4H7017N, as described in International Patent Pub. No. WO/2019/147831

TABLE 8

Binding kinetics of anti-TMPRSS2 mAbs binding to mfTMPRSS2-MMH at 37° C.

| mAb Captured | mAb Capture Level (RU) | 100 nM mfMPRSS2-MMH Bound (RU) | $k_a$ (1/Ms) | $k_d$ (1/s) | $K_D$ (M) | $t^{1/2}$ (min) |
|---|---|---|---|---|---|---|
| Positive control* | 144.7 ± 0.8 | 11.8 | 1.08E ± 07 | 3.96E−02 | 3.66E−09 | 0.3 |
| mAb8021 | 134.4 ± 0.6 | 36.7 | 7.71E ± 06 | 1.09E−04 | 1.41E−11 | 106.3 |
| mAb8029 | 146.0 ± 0.2 | 35.3 | 5.17E ± 06 | 3.92E−04 | 7.58E−11 | 29.5 |

*Positive control antibody H4H7017N, as described in International Patent Pub. No. WO/2019/147831

TABLE 9

Binding kinetics of anti-TMPRSS2 mAbs binding to rTMPRSS2-MMH at 25° C.

| mAb Captured | mAb Capture Level (RU) | 100 nM rTMPRSS2-MMH Bound (RU) | $k_a$ (1/Ms) | $k_d$ (1/s) | $K_D$ (M) | $t^{1/2}$ (min) |
|---|---|---|---|---|---|---|
| Positive control** | 207.6 ± 2.4 | 0.24 | NB* | NB* | NB* | NB* |
| mAb8021 | 300.2 ± 0.9 | −0.31 | NB* | NB* | NB* | NB* |
| mAb8029 | 326.7 ± 1.3 | 41.21 | 1.07E ± 05 | 3.64E−04 | 3.40E−09 | 31.8 |

*No binding was observed under the current experimental conditions
**Positive control antibody H4H7017N, as described in International Patent Pub. No. WO/2019/147831

TABLE 10

Binding kinetics of anti-TMPRSS2 mAbs
binding to rTMPRSS2-MMH at 37° C.

| mAb Captured | mAb Capture Level (RU) | 100 nM rTMPRSS2-MMH Bound (RU) | $k_a$ (1/Ms) | $k_d$ (1/s) | $K_D$ (M) | t½ (min) |
|---|---|---|---|---|---|---|
| Positive control** | 259.6 ± 0.9 | 0.5 | NB* | NB* | NB* | NB* |
| mAb8021 | 365.6 ± 1 | −0.6 | NB* | NB* | NB* | NB* |
| mAb8029 | 404.1 ± 3.7 | 65.4 | 6.82E ± 04 | 1.72E−03 | 2.51E−08 | 6.7 |

*No binding was observed under the current experimental conditions.
**Positive control antibody H4H7017N, as described in International Patent Pub. No. WO/2019/147831

TABLE 11

Binding kinetics of anti-TMPRSS2 mAbs binding
to mTMPRSS2-MMH at 25° C.

| mAb Captured | mAb Capture Level (RU) | 100 nM mTMPRSS2-MMH Bound (RU) | $k_a$ (1/Ms) | $k_d$ (1/s) | $K_D$ (M) | t½ (min) |
|---|---|---|---|---|---|---|
| Positive control** | 204.6 ± 1.6 | −0.81 | NB* | NB* | NB* | NB* |
| mAb8021 | 298.6 ± 0.8 | −0.8 | NB* | NB* | NB* | NB* |
| mAb8029 | 324.2 ± 1 | 41.99 | 1.33E ± 05 | 4.42E−04 | 3.33E−09 | 26.2 |

*No binding was observed under the current experimental conditions.
**Positive control antibody H4H7017N, as described in International Patent Pub. No. WO/2019/147831

TABLE 12

Binding kinetics of anti-TMPRSS2 mAbs binding
to mTMPRSS2-MMH at 37° C.

| mAb Captured | mAb Capture Level (RU) | 100 nM mTMPRSS2-MMH Bound (RU) | $k_a$ (1/Ms) | $k_d$ (1/s) | $K_D$ (M) | t½ (min) |
|---|---|---|---|---|---|---|
| Positive control** | 258.4 ± 2.4 | 0.0 | NB* | NB* | NB* | NB* |
| mAb8021 | 363.0 ± 1.0 | −0.5 | NB* | NB* | NB* | NB* |
| mAb8029 | 402.4 ± 3.3 | 64.7 | 2.14E ± 05 | 2.09E−03 | 9.75E−09 | 5.5 |

*indicates that no binding was observed under the current experimental conditions.
**Positive control antibody H4H7017N, as described in International Patent Pub. No. WO/2019/147831

Example 4: pH Sensitivity of Anti-TMPRSS2 Antibodies

Dissociation rate constant (kd) for TMPRSS2 binding to purified anti-TMPRSS2 monoclonal antibody was determined using a real-time surface plasmon resonance based Biacore T200 biosensor platform. All binding studies were performed at 37° C. using two running buffers, (i) 1.9 mM NaH2PO4, 8.1 mM Na2HPO4, 2.7 mM KCl, 137 mM NaCl, 0.05% v/v Surfactant Tween-20, pH7.4 (PBS-T-pH7.4), and (ii) 8.8 mM NaH2PO4, 1.2 mM Na2HPO4, 2.7 mM KCl, 137 mM NaCl, 0.05% v/v Surfactant Tween-20, pH6.0 (PBS-T-pH6.0). The CM5 Biacore sensor surface derivatized by amine coupling with an anti-human Fc specific mouse mAb was used to capture different anti-TMPRSS2 mAbs. All the TMPRSS2 reagents were expressed with a C-terminal myc-myc-hexahistidine tag (subsequently referred to as TMPRSS2-MMH). Different concentrations of human TMPRSS2-MMH, *Macaca fascicularis* TMPRSS2-MMH, rat TMPRSS2-MMH, or mouse TMPRSS2-MMH prepared in PBS-T-pH7.4 running buffer (25 nM-6.25 nM; 4-fold serial dilution) were injected for 2.5 minutes at a flow rate of 30 μL/minute followed by the dissociation of bound TMPRSS2-MMH proteins in PBS-T-pH7.4 or PBS-T-pH6.0 running buffers for 8 minutes.

Dissociation rate constants (kd) in two running buffers were determined by fitting the real-time binding sensorgrams to a 1:1 binding model using Scrubber 2.0c curve-fitting software.

Values of dissociation rate for anti-TMPRSS2 mAb binding to human TMPRSS2-MMH, monkey TMPRSS2-MMH, rat TMPRSS2-MMH and mouse TMPRSS2-MMH at 37° C. in PBS-T-pH7.4 and PBS-T-pH6.0 are shown in Table 13 through Table 16. None of the antibodies exhibited pH sensitivity.

TABLE 13

Dissociation rate constants of anti-TMPRSS2 mAbs binding to human TMPRSS2-MMH at 37° C. in PBS-T-pH 7.4 and PBS-T-pH 6.0

| | Human TMPRSS2-MMH Binding at 37° C. | | | | | | | | |
|---|---|---|---|---|---|---|---|---|---|
| | pH 7.4 Running Buffer | | | | pH 6.0 Running Buffer | | | | |
| mAb Captured | mAb Capture Level (RU) | 100 nm Ag Bound (RU) | kd (1/s) | t½ (min) | mAb Capture Level (RU) | 100 nm Ag Bound (RU) | kd (1/s) | t½ (min) | t½ Ratio (pH 7.4/ pH 6.0) |
| Positive control* | 332 | 66 | 2.63E−03 | 4 | 320.4 | 67 | 3.05E−03 | 4 | 1.2 |
| mAb8021 | 254.9 | 69 | 1.92E−04 | 60 | 245.9 | 71 | 1.29E−04 | 90 | 0.7 |
| mAb8029 | 368.8 | 82 | 6.24E−04 | 19 | 356.2 | 80 | 6.15E−04 | 19 | 1.0 |

*Positive control antibody H4H7017N, as described in International Patent Pub. No. WO/2019/147831

TABLE 14

Dissociation rate constants of anti-TMPRSS2 mAbs binding to monkey TMPRSS2-MMH at 37° C. in PBS-T-pH 7.4 and PBS-T-pH 6.0

| | Monkey TMPRSS2-MMH Binding at 37° C. | | | | | | | | |
|---|---|---|---|---|---|---|---|---|---|
| | pH 7.4 Running Buffer | | | | pH 6.0 Running Buffer | | | | |
| mAb Captured | mAb Capture Level (RU) | 100 nm Ag Bound (RU) | kd (1/s) | t½ (min) | mAb Capture Level (RU) | 100 nm Ag Bound (RU) | kd (1/s) | t½ (min) | t½ Ratio (pH 7.4/ pH 6.0) |
| Positive control* | 334.7 | 20 | 3.70E−02 | 0.3 | 320.6 | 13 | 4.31E−02 | 0.3 | 1.2 |
| mAb8021 | 253.3 | 71 | 1.27E−04 | 91 | 244.2 | 70 | 1.11E−04 | 104 | 0.9 |
| mAb8029 | 366 | 90 | 4.08E−04 | 28 | 360.1 | 94 | 3.39E−04 | 34 | 0.8 |

*Positive control antibody H4H7017N, as described in International Patent Pub. No. WO/2019/147831

TABLE 15

Dissociation rate constants of anti-TMPRSS2 mAbs binding to rat TMPRSS2-MMH at 37° C. in PBS-T-pH 7.4 and PBS-T-pH 6.0

| | Rat TMPRSS2-MMH Binding at 37° C. | | | | | | | | |
|---|---|---|---|---|---|---|---|---|---|
| | pH 7.4 Running Buffer | | | | pH 6.0 Running Buffer | | | | |
| mAb Captured | mAb Capture Level (RU) | 100 nm Ag Bound (RU) | kd (1/s) | t½ (min) | mAb Capture Level (RU) | 100 nm Ag Bound (RU) | kd (1/s) | t½ (min) | t½ Ratio (pH 7.4/ pH 6.0) |
| Positive control** | 297.2 | 0 | NB* | NB* | 295.7 | 0 | NB* | NB* | NB* |
| mAb8021 | 333.6 | −1 | NB* | NB* | 332.4 | −1 | NB* | NB* | NB* |
| mAb8029 | 340.4 | 70 | 2.02E−03 | 6 | 338.2 | 71 | 2.28E−03 | 5 | 1.1 |

*No binding was observed under the current experimental conditions
**Positive control antibody H4H7017N, as described in International Patent Pub. No. WO/2019/147831

TABLE 16

Dissociation rate constants of anti-TMPRSS2 mAbs binding to mouse TMPRSS2-MMH at 37° C. in PBS-T-pH 7.4 and PBS-T-pH 6.0

| | Mouse TMPRSS2-MMH Binding at 37° C. | | | | | | | | |
|---|---|---|---|---|---|---|---|---|---|
| | pH 7.4 Running Buffer | | | | pH 6.0 Running Buffer | | | | |
| mAb Captured | mAb Capture Level (RU) | 100 nm Ag Bound (RU) | kd (1/s) | t½ (min) | mAb Capture Level (RU) | 100 nm Ag Bound (RU) | kd (1/s) | t½ (min) | t½ Ratio (pH 7.4/ pH 6.0) |
| Positive control** | 330.7 | −1 | NB* | NB* | 317.3 | −1 | NB* | NB* | NB* |

TABLE 16-continued

Dissociation rate constants of anti-TMPRSS2 mAbs binding to mouse TMPRSS2-MMH at 37° C. in PBS-T-pH 7.4 and PBS-T-pH 6.0

Mouse TMPRSS2-MMH Binding at 37° C.

| | pH 7.4 Running Buffer | | | | pH 6.0 Running Buffer | | | | |
| --- | --- | --- | --- | --- | --- | --- | --- | --- | --- |
| mAb Captured | mAb Capture Level (RU) | 100 nm Ag Bound (RU) | kd (1/s) | t½ (min) | mAb Capture Level (RU) | 100 nm Ag Bound (RU) | kd (1/s) | t½ (min) | t½ Ratio (pH 7.4/ pH 6.0) |
| mAb8021 | 251.3 | −2 | NB* | NB* | 244.8 | −1 | NB* | NB* | NB* |
| mAb8029 | 359.9 | 74 | 2.46E−03 | 5 | 360.9 | 74 | 2.57E−03 | 4 | 1.0 |

*No binding was observed under the current experimental conditions.
**Positive control antibody H4H7017N, as described in International Patent Pub. No. WO/2019/147831

Example 5: Octet Cross-Competition Between Anti-TMPRSS2 Monoclonal Antibodies

Binding competition between TMPRSS2 monoclonal antibodies (mAbs) was determined using a real time, label-free bio-layer interferometry (BLI) assay on the Octet HTX biosensor platform (Pall ForteBio Corp.). The entire experiment was performed at 25° C. in 10 mM HEPES, 150 mM NaCl, 0.05% v/v Surfactant Tween-20, 1 mg/mL BSA, 0.02% NaN3, pH7.4 (HBS-P) buffer with the plate shaking at a speed of 1000 rpm. To assess whether two mAbs are able to compete with one another for binding to their respective epitopes on TMPRSS2, the ectodomain of human TMPRSS2-MMH (hTMPRSS2-MMH) was first captured onto anti-penta-His antibody (HIS1K) coated Octet biosensor tips by submerging the biosensor tips for 1.5 minute in wells containing 10 µg/mL solution of hTMPRSS2-MMH. The hTMPRSS2-MMH captured biosensor tips were then saturated with the first TMPRSS2 mAb (subsequently referred to as mAb-1) by dipping into wells containing 50 µg/mL solution of mAb-1 for 5 minutes. The biosensor tips were then subsequently dipped into wells containing 50 µg/mL solution of second TMPRSS2 mAb (subsequently referred to as mAb-2) for 5 minutes. The biosensor tips were washed in HBS-P buffer in between every step of the experiment. The real-time binding response was monitored during the entire course of the experiment and the binding response at the end of every step was recorded. The response of mAb-2 binding to hTMPRSS2-MMH pre-complexed with mAb-1 was compared and competitive/non-competitive behavior of different anti-TMPRSS2 mAbs was determined as shown in Table 17.

Dissociation rate constants (kd) in two running buffers were determined by fitting the real-time binding sensorgrams to a 1:1 binding model using Scrubber 2.0c curve-fitting software.

TABLE 17

Cross-competition between anti-TMPRSS2 mAbs

| mAb-1 | mAb-2 Competing with mAb-1 |
| --- | --- |
| Positive control* | mAb8021 |
| | mAb8029 |
| mAb8021 | Positive control* |
| | mAb8029 |
| mAb8029 | Positive control* |
| | mAb8021 |

*Positive control antibody H4H7017N, as described in International Patent Pub. No. WO/2019/147831

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants to relate to each and every individual publication, database entry (e.g., Genbank sequences or GeneID entries), patent application, or patent identified even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

We claim:

1. An isolated recombinant antibody or antigen-binding fragment thereof that specifically binds to human transmembrane protease, serine 2 (TMPRSS2), wherein the antibody comprises:
   (i) three heavy chain complementarity determining regions (CDRs) (CDR-H1, CDR-H2, and CDR-H3) contained within a heavy chain variable region (HCVR) comprising SEQ ID NO: 2; and three light chain CDRs (CDR-L1, CDR-L2, and CDR-L3) contained within a light chain variable region (LCVR) comprising SEQ ID NO: 10; or
   (ii) three heavy chain CDRs (CDR-H1, CDR-H2, and CDR-H3) contained within an HCVR comprising SEQ ID NO: 22; and three light chain CDRs (CDR-L1, CDR-L2, and CDR-L3) contained within an LCVR comprising SEQ ID NO: 30; or
   (iii) three heavy chain CDRs (CDR-H1, CDR-H2, and CDR-H3) contained within an HCVR comprising SEQ ID NO: 42; and three light chain CDRs (CDR-L1, CDR-L2, and CDR-L3) contained within an LCVR comprising SEQ ID NO: 50.

2. The antibody or antigen-binding fragment thereof of claim 1, wherein said antibody or antigen-binding fragment thereof comprises an HCVR comprising SEQ ID NO: 2; and an LCVR comprising SEQ ID NO: 10.

3. The antibody or antigen-binding fragment thereof of claim 1, comprising:
   (a) an HCVR comprising the CDR-H1, CDR-H2, and CDR-H3 of an immunoglobulin heavy chain that comprises SEQ ID NO: 2; and
   (b) an LCVR comprising the CDR-L1, CDR-L2, and CDR-L3 of an immunoglobulin light chain that comprises SEQ ID NO: 10.

4. The antibody or antigen-binding fragment thereof of claim 1, comprising:
   an HCVR that comprises:
   (a) a CDR-H1 comprising SEQ ID NO: 4,
   (b) a CDR-H2 comprising SEQ ID NO: 6, and
   (c) a CDR-H3 comprising SEQ ID NO: 8; and
   an LCVR that comprises:
   (a) a CDR-L1 comprising SEQ ID NO: 12,
   (b) a CDR-L2 comprising SEQ ID NO: 14, and
   (c) a CDR-L3 comprising SEQ ID NO: 16.

5. The antibody or antigen-binding fragment thereof of claim 4, comprising:
   (a) an HCVR comprising at least 90% amino acid sequence identity to SEQ ID NO: 2; and (b) an LCVR comprising at least 90% amino acid sequence identity to SEQ ID NO: 10.

6. The antibody or antigen-binding fragment thereof of claim 1, comprising:
(a) a heavy chain immunoglobulin that comprises SEQ ID NO: 18; and
(b) a light chain immunoglobulin that comprises SEQ ID NO: 20.

7. The antibody or antigen-binding fragment thereof of claim 1, wherein said antibody or antigen-binding fragment comprises an HCVR comprising SEQ ID NO: 22; and an LCVR comprising ID NO: 30.

8. The antibody or antigen-binding fragment thereof of claim 1, comprising:
(a) an HCVR comprising the CDR-H1, CDR-H2, and CDR-H3 of an immunoglobulin heavy chain that comprises SEQ ID NO: 22; and
(b) an LCVR comprising the CDR-L1, CDR-L2, and CDR-L3 of an immunoglobulin light chain that comprises SEQ ID NO: 30.

9. The antibody or antigen-binding fragment thereof of claim 1, comprising:
an HCVR that comprises:
(a) a CDR-H1 comprising SEQ ID NO: 24,
(b) a CDR-H2 comprising SEQ ID NO: 26, and
(c) a CDR-H3 comprising SEQ ID NO: 28; and
an LCVR that comprises:
(a) a CDR-L1 comprising SEQ ID NO: 32,
(b) a CDR-L2 comprising SEQ ID NO: 34, and
(c) a CDR-L3 comprising SEQ ID NO: 36.

10. The antibody or antigen-binding fragment thereof of claim 9, comprising:
(a) an HCVR comprising at least 90% amino acid sequence identity to SEQ ID NO: 22; and
(b) an LCVR comprising at least 90% amino acid sequence identity to SEQ ID NO: 30.

11. The antibody or antigen-binding fragment thereof of claim 1, comprising:
(a) a heavy chain immunoglobulin that comprises SEQ ID NO: 38; and
(b) a light chain immunoglobulin that comprises SEQ ID NO: 40.

12. The antibody or antigen-binding fragment thereof of claim 1, wherein said antibody or antigen-binding fragment comprises SEQ ID NO: 42; and an LCVR comprising SEQ ID NO: 50.

13. The antibody or antigen-binding fragment thereof of claim 1, comprising:
(a) an HCVR comprising the CDR-H1, CDR-H2, and CDR-H3 of an immunoglobulin heavy chain that comprises SEQ ID NO: 42; and
(b) an LCVR comprising the CDR-L1, CDR-L2, and CDR-L3 of an immunoglobulin light chain that comprises SEQ ID NO: 50.

14. The antibody or antigen-binding fragment thereof of claim 1, comprising:
an HCVR that comprises:
(a) a CDR-H1 comprising SEQ ID NO: 44,
(b) a CDR-H2 comprising SEQ ID NO: 46, and
(c) a CDR-H3 comprising SEQ ID NO: 48; and
an LCVR that comprises:
(a) a CDR-L1 comprising SEQ ID NO: 52,
(b) a CDR-L2 comprising SEQ ID NO: 54, and
(c) a CDR-L3 comprising SEQ ID NO: 56.

15. The antibody or antigen-binding fragment thereof of claim 14, comprising:
(a) an HCVR comprising at least 90% amino acid sequence identity to SEQ ID NO: 42; and
(b) an LCVR comprising at least 90% amino acid sequence identity to SEQ ID NO: 50.

16. The antibody or antigen-binding fragment of claim 1, comprising:
(a) a heavy chain immunoglobulin that comprises SEQ ID NO: 58; and
(b) a light chain immunoglobulin that comprises SEQ ID NO: 60, or an LCVR that comprises SEQ ID NO: 50.

17. The antibody or antigen-binding fragment thereof of claim 1 which is multispecific.

18. The antibody or antigen-binding fragment thereof of claim 1 which comprises one or more of the following properties:
a) inhibits growth of coronavirus in TMPRSS2-expressing cells;
b) inhibits growth of influenza virus in TMPRSS2-expressing cells;
c) binds to the surface of TMPRSS-expressing cells;
d) does not significantly bind to MDCK/Tet-on cells which do not express TMPRSS2;
e) limits spread of coronavirus infection of cells in vitro;
f) limits spread of influenza virus infection of cells in vitro;
g) protects mice engineered to express the human TMPRSS2 protein from death and/or weight loss caused by coronavirus infection; and
h) protects mice engineered to express the human TMPRSS2 protein from death caused by influenza virus infection.

19. A complex comprising the antibody or antigen-binding fragment thereof of claim 1 bound to a TMPRSS2 polypeptide.

20. A method for making the antibody or antigen-binding fragment thereof of claim 1, comprising:
(a) introducing into a host cell one or more polynucleotides encoding said antibody or antigen-binding fragment; and
(b) culturing the host cell under conditions favorable to expression of the one or more polynucleotides.

21. The method of claim 20, further comprising:
(c) isolating the antibody or antigen-binding fragment thereof from the host cell and/or a medium in which the host cell is grown.

22. The method of claim 20, wherein the host cell is a Chinese hamster ovary cell.

23. An antibody or antigen-binding fragment thereof which is a product of the method of claim 20.

24. A polypeptide pair comprising:
(a) a CDR-H1, a CDR-H2, and a CDR-H3 of a V H domain of an antibody or antigen-binding fragment thereof that comprises SEQ ID NO: 2 and a CDR-L1, a CDR-L2, and a CDR-L3 of a V L domain of an immunoglobulin chain that comprises SEQ ID NO: 10;
(b) a CDR-H1, a CDR-H2, and a CDR-H3 of a V H domain of an antibody or antigen-binding fragment thereof that comprises SEQ ID NO: 22 and a CDR-L1, a CDR-L2, and a CDR-L3 of a V L domain of an immunoglobulin chain that comprises SEQ ID NO: 30; or
(c) a CDR-H1, a CDR-H2, and a CDR-H3 of a V H domain of an antibody or antigen-binding fragment thereof that comprises SEQ ID NO: 42 and a CDR-L1, a CDR-L2, and a CDR-L3 of a V L domain of an immunoglobulin chain that comprises SEQ ID NO: 50.

25. A composition comprising:
(i) a first polynucleotide encoding a polypeptide comprising (a) a CDR-H1 comprising SEQ ID NO: 4, (b) a CDR-H2 comprising SEQ ID NO: 6, and (c) a CDR-H3 comprising SEQ ID NO: 8; and a second polynucleotide encoding a polypeptide comprising (a) a CDR-L1 comprising SEQ ID NO: 12, (b) a CDR-L2 comprising SEQ ID NO: 14, and (c) a CDR-L3 comprising SEQ ID NO: 16;
(ii) a first polynucleotide encoding a polypeptide comprising (a) a CDR-H1 comprising SEQ ID NO: 24, (b) a CDR-H2 comprising SEQ ID NO: 26, and (c) a CDR-H3 comprising SEQ ID NO: 28; and a second polynucleotide encoding a polypeptide comprising (a) a CDR-L1 comprising SEQ ID NO: 32, (b) a CDR-L2 comprising SEQ ID NO: 34, and (c) a CDR-L3 comprising SEQ ID NO: 36; or
(iii) a first polynucleotide encoding a polypeptide comprising (a) a CDR-H1 comprising SEQ ID NO: 44, (b) a CDR-H2 comprising SEQ ID NO: 46, and (c) a CDR-H3 comprising SEQ ID NO: 48; and a second polynucleotide encoding a polypeptide comprising (a) a CDR-L1 comprising SEQ ID NO: 52, (b) a CDR-L2 comprising SEQ ID NO: 54, and (c) a CDR-L3 comprising SEQ ID NO: 56.

26. A vector comprising:
(i) a first polynucleotide encoding a polypeptide comprising (a) a CDR-H1 comprising SEQ ID NO: 4, (b) a CDR-H2 comprising SEQ ID NO: 6, and (c) a CDR-H3 comprising SEQ ID NO: 8; and a second polynucleotide encoding a polypeptide comprising (a) a CDR-L1 comprising SEQ ID NO: 12, (b) a CDR-L2 comprising SEQ ID NO: 14, and (c) a CDR-L3 comprising SEQ ID NO: 16;
(ii) a first polynucleotide encoding a polypeptide comprising (a) a CDR-H1 comprising SEQ ID NO: 4, (b) a CDR-H2 comprising SEQ ID NO: 6, and (c) a CDR-H3 comprising SEQ ID NO: 8; and a second polynucleotide encoding a polypeptide comprising (a) a CDR-L1 comprising SEQ ID NO: 12, (b) a CDR-L2 comprising SEQ ID NO: 14, and (c) a CDR-L3 comprising SEQ ID NO: 16; or
(iii) a first polynucleotide encoding a polypeptide comprising (a) a CDR-H1 comprising SEQ ID NO: 44, (b) a CDR-H2 comprising SEQ ID NO: 46, and (c) a CDR-H3 comprising SEQ ID NO: 48; and a second polynucleotide encoding a polypeptide comprising (a) a CDR-L1 comprising SEQ ID NO: 52, (b) a CDR-L2 comprising SEQ ID NO: 54, and (c) a CDR-L3 comprising SEQ ID NO: 56.

27. A host cell comprising the vector of claim 26.

28. A composition or kit comprising the antibody or antigen-binding fragment thereof of claim 1.

29. A pharmaceutical composition comprising the antibody or antigen-binding fragment thereof of claim 1 and a pharmaceutically acceptable carrier.

30. The pharmaceutical composition of claim 29, further comprising a therapeutic agent selected from the group consisting of an anti-viral drug, a vaccine, an antibody or antigen-binding fragment thereof that binds to influenza Group I HA protein, and an antibody or antigen-binding fragment thereof that binds to influenza Group II HA protein.

31. The composition or kit of claim 28, comprising a further therapeutic agent selected from the group consisting of an anti-viral drug, a vaccine, an antibody or antigen-binding fragment thereof that binds to influenza Group I HA protein, and an antibody or antigen-binding fragment thereof that binds to influenza Group II HA protein.

32. The composition or kit of claim 31 wherein the further therapeutic agent is a member selected from the group consisting of: remdesivir, chloroquine, lopinavir, ritonavir, ribavirin, ledipasvir, sofosbuvir, a combination of ledipasvir and sofosbuvir, oseltamivir, zanamivir, ribavirin and interferon-alpha2b, interferon-alpha2a, an anti-cancer agent, and an antibody or antigen-binding fragment thereof that specifically binds to influenza HA or coronavirus spike protein; and/or an antibody or antigen binding fragment thereof selected from the group consisting of H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B; H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B;

H1H18086B; H1H18087B; H1H18088B;
H1H18089B; H1H18090B; H1H18091B;
H1H18092B; H1H18093B; H1H18094B;
H1H18095B; H1H18096B; H1H18097B;
H1H18098B; H1H18099B; H1H18100B;
H1H18101B; H1H18102B; H1H18103B;
H1H18104B; H1H18105B; H1H18107B;
H1H18108B; H1H18109B; H1H18110B;
H1H18111B; H1H18112B; H1H18113B; H1H18114B;
H1H18115B; H1H18116B; H1H18117B;
H1H18118B; H1H18119B; H1H18120B;
H1H18121B; H1H18122B; H1H18123B;
H1H18124B; H1H18125B; H1H18126B;
H1H18127B; H1H18128B; H1H18129B;
H1H18130B; H1H18131B; H1H18132B;
H1H18133B; H1H18134B; H1H18135B;
H1H18136B; H1H18137B; H1H18138B;
H1H18139B; H1H18140B; H1H18141B;
H1H18142B; H1H18143B; H1H18144B;
H1H18145B; H1H18146B; H1H18147B;
H1H18148B; H1H18149B; H1H18150B;
H1H18151B; H1H18152B; H1H18153B;
H1H18154B; H1H18155B; H1H18156B;
H1H18157B; H1H18158B; H1H18159B;
H1H18160B; H1H18161B; H1H18162B;
H1H18163B; H1H18164B; H1H18165B;
H1H18166B; H1H18167B; H1H18168B;
H1H18169B; H1H18170B; H1H18171B;
H1H18172B; H1H18173B; H1H18174B;
H1H18175B; H1H18176B; H1H18177B;
H1H18178B; H1H18179B; H1H18180B;
H1H18181B; H1H18182B; H1H18183B;
H1H18184B; H1H18185B; H1H18186B;
H1H18187B; H1H18188B; H1H18189B;
H1H18190B; H1H18191B; H1H18192B;
H1H18193B; H1H18194B; H1H18195B;
H1H18196B; H1H18197B; H1H18198B;
H1H18199B; H1H18200B; H1H18201B;
H1H18202B; H1H18203B; H1H18204B;
H1H18205B; H1H18206B; H1H18207B;
H1H18208B; H1H18209B; H1H18210B;
H1H18211B; H1H18212B; H1H18213B;
H1H18214B; H1H18216B; H1H18217B;
H1H18218B; H1H18219B; H1H18220B;
H1H18221B; H1H18222B; H1H18223B;
H1H18224B; H1H18225B; H1H18226B;
H1H18227B; H1H18228B; H1H18229B;
H1H18230B; H1H18231B; H1H18232B;
H1H18233B; H1H18234B; H1H18235B;
H1H18236B; H1H18237B; H1H18238B;
H1H18239B; H1H18240B; H1H18241B;
H1H18242B; H1H18243B; H1H18244B;
H1H18245B; H1H18246B; H1H18247B;
H1H18248B; H1H18249B; H1H18250B;
H1H18251B; H1H18252B; H1H18253B;
H1H18254B; H1H18255B; H1H18256B;
H1H18257B; H1H18258B; H1H18259B;
H1H18261B; H1H18262B; H1H18263B;
H1H18264B; H1H18265B; H1H18266B;
H1H18267B; H1H18268B; H1H18269B;
H1H18270B; H1H18271B; H1H18272B;
H1H18274B; H1H18275B; H1H18276B;
H1H18277B; H1H18278B; H1H18279B;
H1H18280B; H1H18281B; H1H18282B;
H1H18283B; H1H18284B; H1H18285B;
H1H18286B; H1H18287B; H1H18288B;
H1H18289B; H1H18290B; H1H18291B;
H1H18292B; H1H18293B; H1H18294B;
H1H18295B; H1H18297B; H1H18298B;
H1H18299B; H1H18300B; H1H18301B;
H1H18302B; H1H18303B; H1H18304B;
H1H18305B; H1H18306B; H1H18307B;
H1H18308B; H1H18309B; H1H18310B;
H1H18311B; H1H18312B; H1H18313B;
H1H18314B; H1H18315B; H1H18316B;
H1H18317B; H1H18318B; H1H18319B;
H1H18320B; H1H18321B; H1H18322B;
H1H18323B; H1H18324B; H1H18325B;
H1H18326B; H1H18327B; H1H18328B;
H1H18329B; H1H18330B; H1H18331B;
H1H18332B; H1H18333B; H1H18334B;
H1H18335B; H4sH15188P; H1H15188P;
H1H15211P; H1H15177P; H4sH15211P;
H1H15260P2; H1H15259P2; H1H15203P;
H4sH15260P2; H4sH15231P2; H1H15237P2;
H1H15208P; H1H15228P2; H1H15233P2;
H1H15264P2; H1H15231P2; H1H15253P2;
H1H15215P; and H1H15249P2.

33. A vessel or injection device comprising the antibody or antigen-binding fragment thereof of claim 1.

34. A method for treating prostate, renal, or pancreatic cancer or infection with an influenza virus, coronavirus, SARS-CoV, MERS-CoV, SARS-CoV-2, or parainfluenza virus in a subject in need thereof, comprising administering a therapeutically effective amount of the antibody or antigen-binding fragment thereof of claim 1.

35. The method of claim 34, wherein the subject is administered one or more further therapeutic agents selected from the group consisting of an anti-viral drug, a vaccine, an antibody or antigen-binding fragment thereof that binds to influenza Group I HA protein, and an antibody or antigen-binding fragment thereof that binds to influenza Group II HA protein.

36. The method of claim 35, wherein the subject is administered one or more further therapeutic agents which is an anti-viral drug or a vaccine.

37. The method of claim 35, wherein the subject is administered one or more further therapeutic agents which is a member selected from the group consisting of: remdesivir, chloroquine, lopinavir, ritonavir, ribavirin, ledipasvir, sofosbuvir, a combination of ledipasvir and sofosbuvir, oseltamivir, zanamivir, ribavirin and interferon-alpha2b, interferon-alpha2a, and an antibody or antigen-binding fragment thereof that specifically binds to influenza HA or coronavirus spike protein; and/or an antibody or antigen binding fragment thereof selected from the group consisting of H1H11723P; H1H11729P; H1H11820N; H1H11829N; H1H11829N2; H2aM11829N; H2M11830N; H1H11830N2; H1H11903N; H1H14571N; H2a14571N; H1H11704P; H1H11711P; H1H11714P; H1H11717P; H1H11724P; H1H11727P; H1H11730P2; H1H11731P2; H1H11734P2; H1H11736P2; H1H11742P2; H1H11744P2; H1H11745P2; H1H11747P2; H1H11748P2; H1H17952B; H1H17953B; H1H17954B; H1H17955B; H1H17956B; H1H17957B; H1H17958B; H1H17959B; H1H17960B; H1H17961B; H1H17962B; H1H17963B; H1H17964B; H1H17965B; H1H17966B; H1H17967B; H1H17968B; H1H17969B; H1H17970B; H1H17971B; H1H17972B; H1H17973B; H1H17974B; H1H17975B; H1H17976B; H1H17977B; H1H17978B; H1H17979B; H1H17980B; H1H17981B; H1H17982B; H1H17983B; H1H17984B; H1H17985B; H1H17986B; H1H17987B; H1H17988B; H1H17989B; H1H17990B; H1H17991B; H1H17992B; H1H17993B; H1H17994B; H1H17995B; H1H17996B;

H1H17997B; H1H17998B; H1H17999B; H1H18000B; H1H18001B; H1H18002B; H1H18003B; H1H18004B; H1H18005B; H1H18006B; H1H18007B; H1H18008B; H1H18009B; H1H18010B; H1H18011B; H1H18012B; H1H18013B; H1H18014B; H1H18015B; H1H18016B; H1H18017B; H1H18018B; H1H18019B; H1H18020B; H1H18021B; H1H18022B; H1H18023B; H1H18024B; H1H18025B; H1H18026B; H1H18027B; H1H18028B; H1H18029B; H1H18030B; H1H18031B; H1H18032B; H1H18033B; H1H18034B; H1H18035B; H1H18037B; H1H18038B; H1H18039B; H1H18040B; H1H18041B; H1H18042B; H1H18043B; H1H18044B; H1H18045B; H1H18046B; H1H18047B; H1H18048B; H1H18049B; H1H18051B; H1H18052B; H1H18053B; H1H18054B; H1H18055B; H1H18056B; H1H18057B; H1H18058B; H1H18059B; H1H18060B; H1H18061B; H1H18062B; H1H18063B; H1H18064B; H1H18065B; H1H18066B; H1H18067B; H1H18068B; H1H18069B; H1H18070B; H1H18071B; H1H18072B; H1H18073B; H1H18074B; H1H18075B; H1H18076B; H1H18077B; H1H18078B; H1H18079B; H1H18080B; H1H18081B; H1H18082B; H1H18083B; H1H18084B; H1H18085B; H1H18086B; H1H18087B; H1H18088B; H1H18089B; H1H18090B; H1H18091B; H1H18092B; H1H18093B; H1H18094B; H1H18095B; H1H18096B; H1H18097B; H1H18098B; H1H18099B; H1H18100B; H1H18101B; H1H18102B; H1H18103B; H1H18104B; H1H18105B; H1H18107B; H1H18108B; H1H18109B; H1H18110B; H1H18111B; H1H18112B; H1H18113B; H1H18114B; H1H18115B; H1H18116B; H1H18117B; H1H18118B; H1H18119B; H1H18120B; H1H18121B; H1H18122B; H1H18123B; H1H18124B; H1H18125B; H1H18126B; H1H18127B; H1H18128B; H1H18129B; H1H18130B; H1H18131B; H1H18132B; H1H18133B; H1H18134B; H1H18135B; H1H18136B; H1H18137B; H1H18138B; H1H18139B; H1H18140B; H1H18141B; H1H18142B; H1H18143B; H1H18144B; H1H18145B; H1H18146B; H1H18147B; H1H18148B; H1H18149B; H1H18150B; H1H18151B; H1H18152B; H1H18153B; H1H18154B; H1H18155B; H1H18156B; H1H18157B; H1H18158B; H1H18159B; H1H18160B; H1H18161B; H1H18162B; H1H18163B; H1H18164B; H1H18165B; H1H18166B; H1H18167B; H1H18168B; H1H18169B; H1H18170B; H1H18171B; H1H18172B; H1H18173B; H1H18174B; H1H18175B; H1H18176B; H1H18177B; H1H18178B; H1H18179B; H1H18180B; H1H18181B; H1H18182B; H1H18183B; H1H18184B; H1H18185B; H1H18186B; H1H18187B; H1H18188B; H1H18189B; H1H18190B; H1H18191B; H1H18192B; H1H18193B; H1H18194B; H1H18195B; H1H18196B; H1H18197B; H1H18198B; H1H18199B; H1H18200B; H1H18201B; H1H18202B; H1H18203B; H1H18204B; H1H18205B; H1H18206B; H1H18207B; H1H18208B; H1H18209B; H1H18210B; H1H18211B; H1H18212B; H1H18213B; H1H18214B; H1H18216B; H1H18217B; H1H18218B; H1H18219B; H1H18220B; H1H18221B; H1H18222B; H1H18223B; H1H18224B; H1H18225B; H1H18226B; H1H18227B; H1H18228B; H1H18229B; H1H18230B; H1H18231B; H1H18232B; H1H18233B; H1H18234B; H1H18235B; H1H18236B; H1H18237B; H1H18238B; H1H18239B; H1H18240B; H1H18241B; H1H18242B; H1H18243B; H1H18244B; H1H18245B; H1H18246B; H1H18247B; H1H18248B; H1H18249B; H1H18250B; H1H18251B; H1H18252B; H1H18253B; H1H18254B; H1H18255B; H1H18256B; H1H18257B; H1H18258B; H1H18259B; H1H18261B; H1H18262B; H1H18263B; H1H18264B; H1H18265B; H1H18266B; H1H18267B; H1H18268B; H1H18269B; H1H18270B; H1H18271B; H1H18272B; H1H18274B; H1H18275B; H1H18276B; H1H18277B; H1H18278B; H1H18279B; H1H18280B; H1H18281B; H1H18282B; H1H18283B; H1H18284B; H1H18285B; H1H18286B; H1H18287B; H1H18288B; H1H18289B; H1H18290B; H1H18291B; H1H18292B; H1H18293B; H1H18294B; H1H18295B; H1H18297B; H1H18298B; H1H18299B; H1H18300B; H1H18301B; H1H18302B; H1H18303B; H1H18304B; H1H18305B; H1H18306B; H1H18307B; H1H18308B; H1H18309B; H1H18310B; H1H18311B; H1H18312B; H1H18313B; H1H18314B; H1H18315B; H1H18316B; H1H18317B; H1H18318B; H1H18319B; H1H18320B; H1H18321B; H1H18322B; H1H18323B; H1H18324B; H1H18325B; H1H18326B; H1H18327B; H1H18328B; H1H18329B; H1H18330B; H1H18331B; H1H18332B; H1H18333B; H1H18334B; H1H18335B; H4sH15188P; H1H15188P; H1H15211P; H1H15177P; H4sH15211P; H1H15260P2; H1H15259P2; H1H15203P; H4sH15260P2; H4sH15231P2; H1H15237P2; H1H15208P; H1H15228P2; H1H15233P2; H1H15264P2; H1H15231P2; H1H15253P2; H1H15215P; and H1H15249P2.

38. A method for administering the antibody or antigen-binding fragment thereof of claim 1 into the body of a subject comprising injecting the antibody or antigen-binding fragment thereof into the body of the subject.

39. The method of claim 38, wherein the antibody or antigen-binding fragment thereof is injected into the body of the subject subcutaneously, intravenously or intramuscularly.

40. The antibody or antigen-binding fragment thereof of claim 1, which binds to TMPRSS2 with an $EC_{50}$ of less than about $10^{-9}$ M.

41. The antibody or antigen-binding fragment thereof of claim 1, which demonstrates an increase in survival in a coronavirus-infected animal after administration to said coronavirus-infected animal, as compared to a comparable coronavirus-infected animal without said administration.

42. The antibody or antigen-binding fragment thereof of claim 4 which is an antibody comprising:
   (i) a heavy chain comprising at least about 90% sequence identity to the heavy chain comprising SEQ ID NO: 18; and a light chain comprising least about 90% sequence identity to the light chain comprising SEQ ID NO: 20.

43. The antibody or antigen-binding fragment thereof of claim 9 which is an antibody comprising:
   (ii) a heavy chain comprising at least about 90% sequence identity to the heavy chain comprising SEQ ID NO: 38; and a light chain comprising least about 90% sequence identity to the light chain comprising SEQ ID NO: 40.

44. The antibody or antigen-binding fragment thereof of claim 14 which is an antibody comprising:
   (iii) a heavy chain comprising at least about 90% sequence identity to the heavy chain comprising SEQ ID NO: 58; and a light chain comprising at least about 90% sequence identity to the light chain comprising SEQ ID NO: 60.

\* \* \* \* \*